US012760069B2

(12) United States Patent
Roughton et al.

(10) Patent No.: US 12,760,069 B2
(45) Date of Patent: Oct. 13, 2026

(54) COMPOUNDS TARGETING ALPHA4-BETA7 INTEGRIN

(71) Applicant: ZEALAND PHARMA A/S, Søborg (DK)

(72) Inventors: Andrew Roughton, Boston, MA (US); Narendrakumar Patel, Brampton (CA); Adam Paul Kafal, Toronto (CA); Manuel Perez Vazquez, Milton (CA); Jennifer Hickey, Fords, NJ (US); Sai Kumar Chakka, Dorval (CA); Monzur Morshed, Mississauga (CA)

(73) Assignee: Zealand Pharma A/S, Søborg (DK)

( * ) Notice: Subject to any disclaimer, the term of this patent is extended or adjusted under 35 U.S.C. 154(b) by 856 days.

(21) Appl. No.: 18/011,997

(22) PCT Filed: Jun. 25, 2021

(86) PCT No.: PCT/EP2021/067469
§ 371 (c)(1),
(2) Date: Dec. 21, 2022

(87) PCT Pub. No.: WO2022/002781
PCT Pub. Date: Jan. 6, 2022

(65) Prior Publication Data

US 2023/0295235 A1 Sep. 21, 2023

(30) Foreign Application Priority Data

Jun. 29, 2020 (EP) .................................... 20182792
Feb. 17, 2021 (EP) .................................... 21157715

(51) Int. Cl.
*C07K 7/56* (2006.01)
*A61P 1/00* (2006.01)

(52) U.S. Cl.
CPC . *C07K 7/56* (2013.01); *A61P 1/00* (2018.01)

(58) Field of Classification Search
CPC .................................... C07K 7/56; A61P 1/00
See application file for complete search history.

(56) References Cited

FOREIGN PATENT DOCUMENTS

WO WO-2017/079821 A1 5/2017
WO WO-2018/085921 A1 5/2018
WO WO-2018205008 A1 * 11/2018 ............... C07K 7/56

OTHER PUBLICATIONS

Greene, T. W. et al., "Protective Groups in Organic Synthesis", John Wiley & Sons, Inc., 3rd Edition, Cover Page—6 pages (1999).
Greene, T. W. et al., "Protective Groups in Organic Synthesis", John Wiley & Sons, Inc., 3rd Edition, Chapter 2, 231 pages (1999).
Greene, T. W. et al., "Protective Groups in Organic Synthesis", John Wiley & Sons, Inc., 3rd Edition, Chapter 5, 87 pages (1999).
Greene, T. W. et al., "Protective Groups in Organic Synthesis", John Wiley & Sons, Inc., 3rd Edition, Chapter 7, 162 pages (1999).
Kates, S. A. et al., "Solid-Phase Synthesis", A Practical Guide, Marcel Dekker, Inc., Chapter 1, 87 pages (2000).
Kates, S. A. et al., "Solid-Phase Synthesis", A Practical Guide, Marcel Dekker, Inc., Chapter 2, 28 pages (2000).
Kates, S. A. et al., "Solid-Phase Synthesis", A Practical Guide, Marcel Dekker, Inc., Chapter 3, 30 pages (2000).
Kates, S. A. et al., "Solid-Phase Synthesis", A Practical Guide, Marcel Dekker, Inc., Chapter 4, 71 pages (2000).
Kates, S. A. et al., "Solid-Phase Synthesis", A Practical Guide, Marcel Dekker, Inc., Chapter 5, 81 pages (2000).
Kates, S. A. et al., "Solid-Phase Synthesis", A Practical Guide, Marcel Dekker, Inc., Chapter 6, 60 pages (2000).

(Continued)

*Primary Examiner* — Amber D Steele
(74) *Attorney, Agent, or Firm* — MARSHALL, GERSTEIN & BORUN LLP

(57) ABSTRACT

Compounds of formula (I) and pharmaceutically acceptable salts and solvates thereof, are described. The compounds are α4β7 antagonists and are useful in the prevention or treatment of inflammatory conditions and/or autoimmune diseases, especially inflammatory bowel disease.

(I)

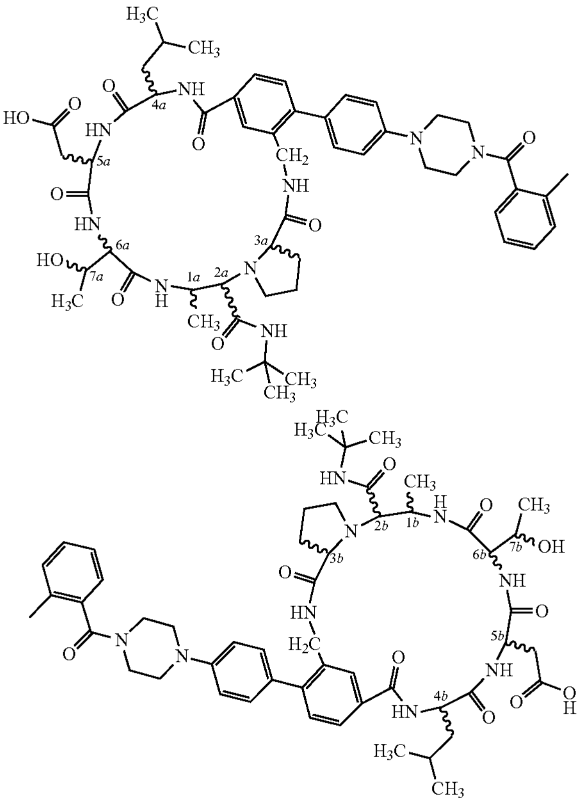

18 Claims, 9 Drawing Sheets

(56) References Cited

OTHER PUBLICATIONS

Kates, S. A. et al., "Solid-Phase Synthesis", A Practical Guide, Marcel Dekker, Inc., Chapter 7, 38 pages (2000).
International Search Report and Written Opinion in PCT/EP2021/067469, mailed by the European Patent Office on Oct. 20, 2021 (8 pages).
International Preliminary Report on Patentability and Written Opinion of the International Searching Authority in International Application No. PCT/EP2021/067469, dated Dec. 13, 2022 (6 pages).

* cited by examiner

Chemical Formula: $C_{100}H_{129}N_{17}O_{18}{}^{2}$
Exact Mass: 1855.97

Chemical Formula: $C_{87}H_{106}N_{14}O_{16}^{2\cdot}$
Exact Mass: 1602.79

Chemical Formula: $C_{91}H_{114}N_{16}O_{18}^{3\cdot}$
Exact Mass: 1718.85

Chemical Formula: $C_{84}H_{101}N_{13}O_{14}^{2-}$
Exact Mass: 1515.76

Chemical Formula: $C_{20}H_{35}N_5O_6^{2-}$
Exact Mass: 441.26

COMPOUNDS TARGETING ALPHA4-BETA7 INTEGRIN

FIELD OF THE INVENTION

This invention relates to novel compounds. The invention also relates to their preparation, and their use in the treatment of a number of conditions mediated by α4β7 integrin, particularly although not exclusively inflammatory conditions and/or autoimmune diseases, such as inflammatory bowel diseases.

BACKGROUND TO THE INVENTION

Integrins are transmembrane receptors that are the bridges for cell-cell and cell-extracellular matrix (ECM) interactions. When triggered, integrins trigger chemical pathways to the interior (signal transduction), such as the chemical composition and mechanical status of the ECM.

Integrins are obligate heterodimers, having two different chains: the α (alpha) and β (beta) subunits. The α4β7 integrin is expressed on lymphocytes and is responsible for T-cell homing into gut-associated lymphoid tissues through its binding to mucosal addressin cell adhesion molecule (MAdCAM), which is present on high endothelial venules of mucosal lymphoid organs.

Inhibitors of specific integrin-ligand interactions have been shown effective as anti-inflammatory agents for the treatment of various autoimmune diseases. For example, monoclonal antibodies displaying high binding affinity for α4β7 have displayed therapeutic benefits for gastrointestinal auto-inflammatory/autoimmune diseases, such as Crohn's disease, and ulcerative colitis.

There is a need to develop improved α4β7 antagonists to prevent or treat inflammatory conditions and/or autoimmune diseases.

SUMMARY OF THE INVENTION

In one aspect of the invention, there is provided a compound of formula (I):

In another aspect, the invention provides a pharmaceutical composition comprising the compound of formula (I), or a pharmaceutically acceptable salt or solvate thereof, and a pharmaceutically acceptable carrier.

In another aspect, the invention provides the compound of formula (I), or a pharmaceutically acceptable salt or solvate thereof, for use as a medicament.

In another aspect, the invention provides the compound of formula (I), or a pharmaceutically acceptable salt or solvate thereof, for use in treating an inflammatory condition and/or an autoimmune disease in a patient.

In another aspect, the invention provides use of the compound of formula (I), or a pharmaceutically acceptable salt or solvate thereof, in the manufacture of a medicament for treating an inflammatory condition and/or an autoimmune disease in a patient.

In another aspect, the invention provides a method of treating an inflammatory condition and/or an autoimmune disease in a patient in need thereof, the method comprising administration of the compound of formula (I), or a pharmaceutically acceptable salt or solvate thereof, to the patient.

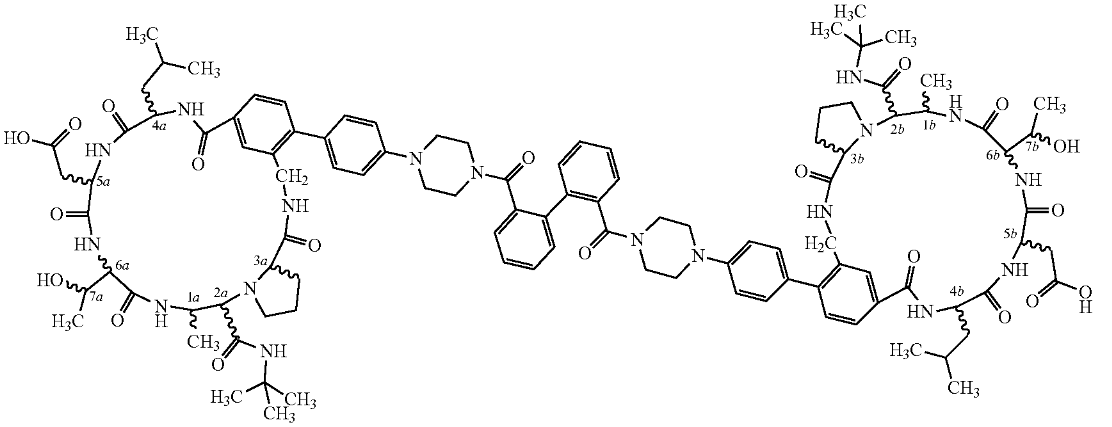

or a pharmaceutically acceptable salt or solvate thereof, wherein the stereochemistry of the carbon atom at each of positions 1a, 1b, 2a, 2b, 3a, 3b, 4a, 4b, 5a, 5b, 6a, 6b, 7a and 7b may each be independently (R) or (S).

Figure 7:
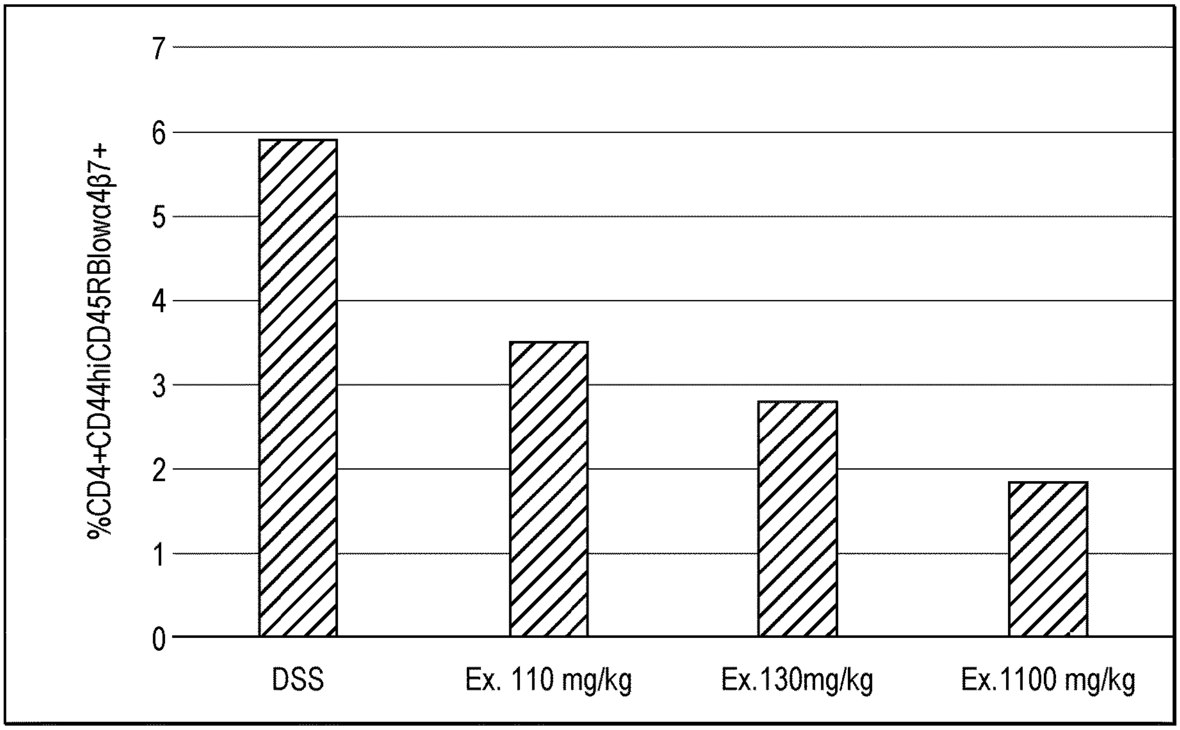

FIG. 7 shows the inhibition of integrin α4β7+ T cell infiltration into mesenterial lymph nodes by the compound of Example 1 administered at 10, 30 or 100 mg/kg in comparison to DSS alone.

Figure 8:
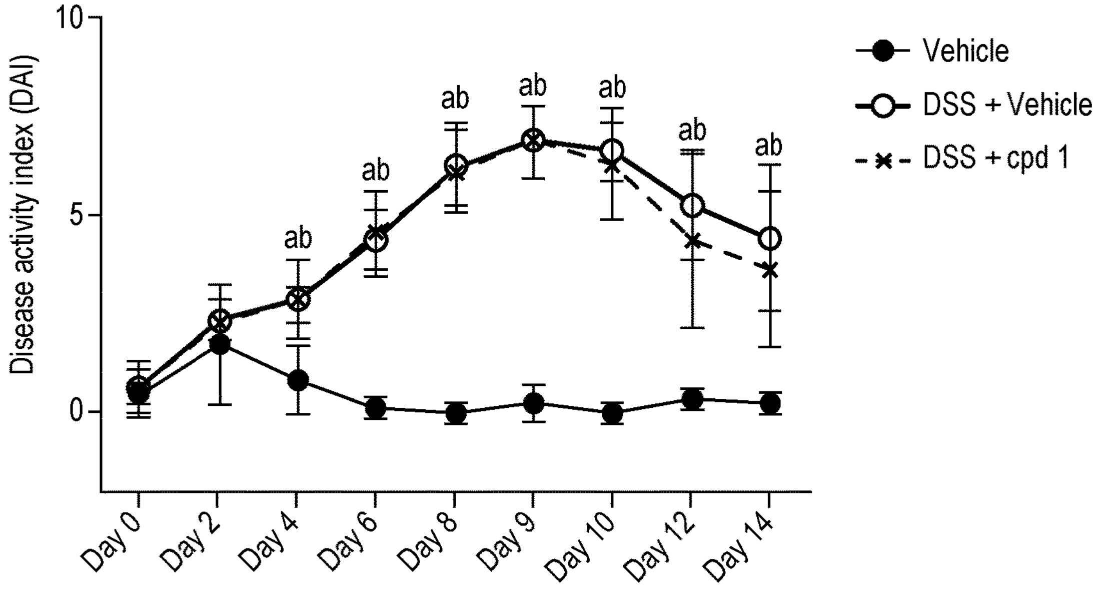

FIG. 8 shows DAI score is expressed as mean±SD for each group in example 4.

Figure 9:
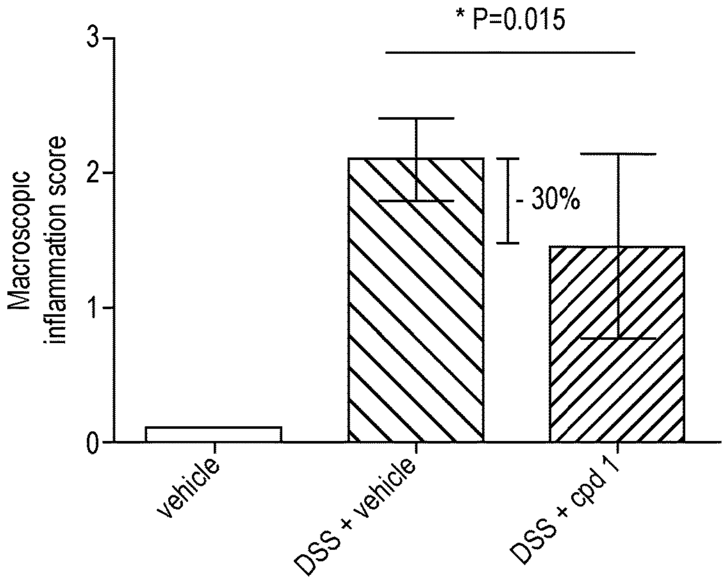

FIG. 9 shows Macroscopic inflammation score calculated for the different groups of DSS induced UC mice, receiving the vehicle or the treatments in example 4.

Figure 10:
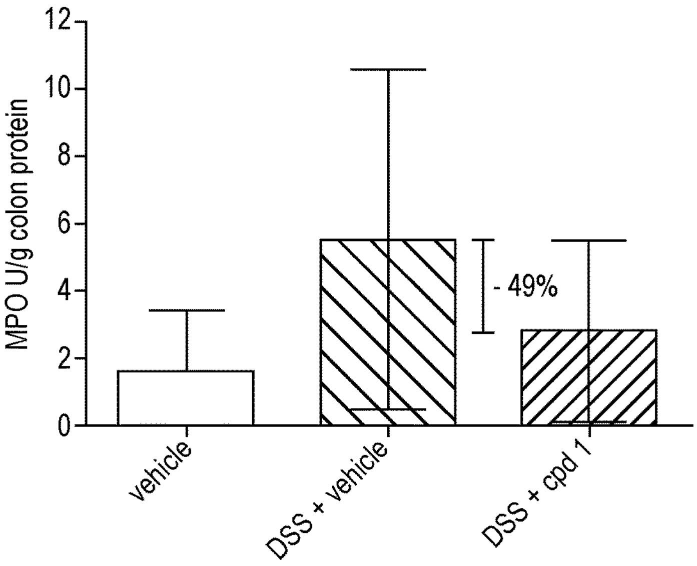

FIG. 10 shows MPO activity from medio-distal part of the colon in example 4.

DETAILED DESCRIPTION

In one aspect of the invention, there is provided a compound of formula (I), as defined above, or a pharmaceutically acceptable salt or solvate thereof. In this specification all references to compounds of formula (I) generally include references to pharmaceutically acceptable salts and solvates thereof.

Included within the scope of the present invention are all stereoisomers, geometric isomers and tautomeric forms of the compounds of formula (I), including compounds exhibiting more than one type of isomerism, and mixtures of one or more thereof.

In the compound of formula (I), the stereochemistry of the carbon atom at each of the positions 1a, 1b, 2a, 2b, 3a, 3b, 4a, 4b, 5a, 5b, 6a, 6b, 7a and 7b may each be independently (R) or (S).

In one embodiment, the stereochemistry of the carbon atom at position 1a is (S). In one embodiment, the stereochemistry of the carbon atom at position 1a is (R). In one embodiment, the stereochemistry of the carbon atom at position 1b is (S). In one embodiment, the stereochemistry of the carbon atom at position 1b is (R). In one embodiment, the stereochemistry of the carbon atom at position 2a is (S). In one embodiment, the stereochemistry of the carbon atom at position 2a is (R). In one embodiment, the stereochemistry of the carbon atom at position 4b is (S). In one embodiment, the stereochemistry of the carbon atom at position 4b is (R). In one embodiment, the stereochemistry of the carbon atom at position 5a is (S). In one embodiment, the stereochemistry of the carbon atom at position 5a is (R). In one embodiment, the stereochemistry of the carbon atom at position 5b is (S). In one embodiment, the stereochemistry of the carbon atom at position 5b is (R). In one embodiment, the stereochemistry of the carbon atom at position 6a is (S). In one embodiment, the stereochemistry of the carbon atom at position 6a is (R). In one embodiment, the stereochemistry of the carbon atom at position 6b is (S). In one embodiment, the stereochemistry of the carbon atom at position 6b is (R). In one embodiment, the stereochemistry of the carbon atom at position 7a is (S). In one embodiment, the stereochemistry of the carbon atom at position 7a is (R). In one embodiment, the stereochemistry of the carbon atom at position 7b is (S). In one embodiment, the stereochemistry of the carbon atom at position 7b is (R).

In one embodiment, the stereochemistry of the carbon atom at each of positions 1a and 1b is (S). In one embodiment, the stereochemistry of the carbon atom at each of positions 2a and 2b is (S). In one embodiment, the stereochemistry of the carbon atom at each of positions 3a and 3b is (S). In one embodiment, the stereochemistry of the carbon atom at each of positions 4a and 4b is (S). In one embodiment, the stereochemistry of the carbon atom at each of positions 5a and 5b is (S). In one embodiment, the stereochemistry of the carbon atom at each of positions 6a and 6b is (S). In one embodiment, the stereochemistry of the carbon atom at each of positions 7a and 7b is (R).

In a preferred embodiment, there is provided a compound of formula (Ia):

(Ia)

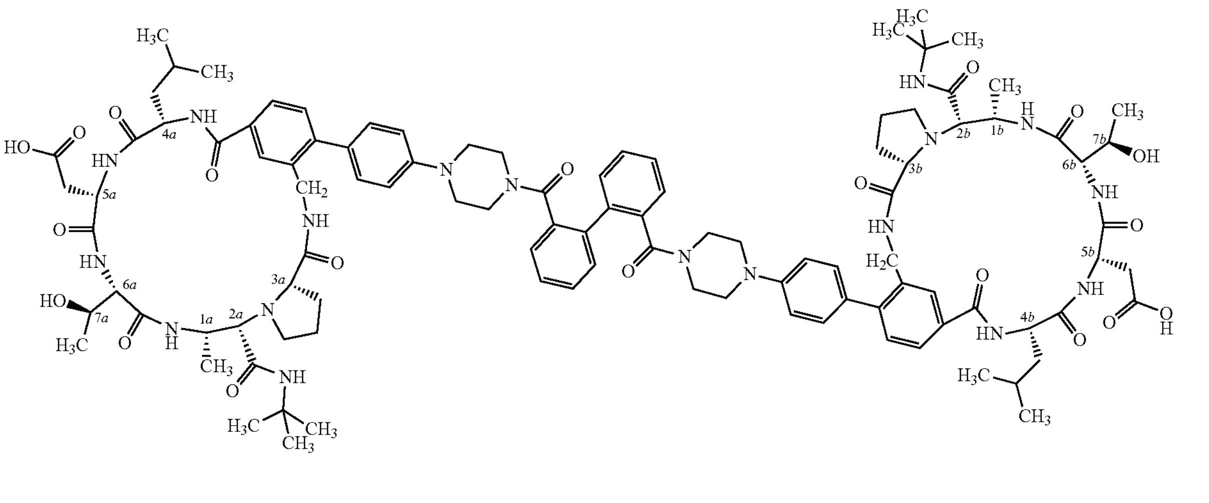

istry of the carbon atom at position 2b is (S). In one embodiment, the stereochemistry of the carbon atom at position 2b is (R). In one embodiment, the stereochemistry of the carbon atom at position 3a is (S). In one embodiment, the stereochemistry of the carbon atom at position 3a is (R). In one embodiment, the stereochemistry of the carbon atom at position 3b is (S). In one embodiment, the stereochemistry of the carbon atom at position 3b is (R). In one embodiment, the stereochemistry of the carbon atom at position 4a is (S). In one embodiment, the stereochemistry of the carbon atom at position 4a is (R). In one embodiment, the stereochem- or pharmaceutically acceptable salt or solvate thereof. In the compound of formula (Ia), the stereochemistry of the carbon atom at all of the positions 1a, 1b, 2a, 2b, 3a, 3b, 4a, 4b, 5a, 5b, 6a, and 6b in formula (I) is (S) and the stereochemistry of the carbon atom at the positions 7a and 7b is (R).

Salts, Solvates, Isotopically Labelled Compounds, Polymorphs

In certain embodiments, there is provided according to the invention pharmaceutically acceptable salts of the compounds described herein. The term "pharmaceutically acceptable salt" as used herein, represents salts or zwitterionic forms of the compounds of the present invention which are water or oil-soluble or dispersible, which are suitable for treatment of diseases without undue toxicity, irritation, and allergic response; which are commensurate with a reasonable benefit/risk ratio, and which are effective for their intended use. The salts can be prepared during the final isolation and purification of the compounds or separately by treatment of the compound with a suitable acid, such that one or more nitrogen atoms is protonated, or with a suitable base, such that one or more carboxylic acid groups is deprotonated.

Representative acid addition salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, fumarate, hydrochloride, hydrobromide, hydroiodide, 2-hydroxyethanesulfonate (isethionate), lactate, maleate, mesitylenesulfonate, methanesulfonate, naphthylenesulfonate, nicotinate, 2-naphthalenesulfonate, oxalate, pamoate, pectinate, persulfate, 3-phenylproprionate, picrate, pivalate, propionate, succinate, tartrate, trichloroacetate, trifluoroacetate, phosphate, glutamate, bicarbonate, para-toluenesulfonate, and undecanoate.

Representative base addition salts include the sodium, potassium, magnesium, calcium, aluminium, zinc, ammonium, arginine, benzathine, choline, diethylamine, diolamine, glycine, lysine, meglumine, olamine, and tromethamine salts.

Examples of acids which can be employed to form therapeutically acceptable addition salts include inorganic acids such as hydrochloric, hydrobromic, sulfuric, and phosphoric, and organic acids such as oxalic, maleic, succinic, and citric. Examples of bases which can be employed to form therapeutically acceptable addition salts include metal oxides or hydroxides including sodium, potassium, magnesium or calcium hydroxide, ammonia or amines such as diethylamine, or amino acids such as glycine or lysine. In certain embodiments, any of the peptide compounds described herein are salt forms, e.g., acetate salts.

The compounds of the invention may also exist in unsolvated and solvated forms. The term 'solvate' is used herein to describe a molecular complex comprising the compound of the invention and one or more pharmaceutically acceptable solvent molecules, for example, ethanol. The term 'hydrate' is employed when said solvent is water.

The compounds of the invention include compounds of formula (I) as hereinbefore defined, including all polymorphs and crystal habits thereof, prodrugs and isomers thereof (including optical, geometric and tautomeric isomers) as hereinafter defined and isotopically-labelled compounds of formula (I).

The compounds of the invention may exist in a continuum of solid states ranging from fully amorphous to fully crystalline. The term 'amorphous' refers to a state in which the material lacks long range order at the molecular level and, depending upon temperature, may exhibit the physical properties of a solid or a liquid. Typically such materials do not give distinctive X-ray diffraction patterns and, while exhibiting the properties of a solid, are more formally described as a liquid. Upon heating, a change from solid to liquid properties occurs which is characterised by a change of state, typically second order ('glass transition'). The term 'crystalline' refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterised by a phase change, typically first order ('melting point').

The present invention includes all pharmaceutically acceptable isotopically-labelled compounds of formula (I) wherein one or more atoms are replaced by atoms having the same atomic number, but an atomic mass or mass number different from the atomic mass or mass number which predominates in nature. Examples of isotopes suitable for inclusion in the compounds of the invention include isotopes of hydrogen, such as $^{2}H$ and $^{3}H$, carbon, such as $^{11}C$, $^{13}C$ and $^{14}C$, nitrogen, such as $^{13}N$ and $^{15}N$, and oxygen, such as $^{15}O$, $^{17}O$ and $^{18}O$.

Certain isotopically-labelled compounds of formula (I), for example, those incorporating a radioactive isotope, are useful in drug and/or substrate tissue distribution studies. The radioactive isotopes tritium, i.e. $^{3}H$, and carbon-14, i.e. $^{14}C$, are particularly useful for this purpose in view of their ease of incorporation and ready means of detection.

Substitution with heavier isotopes such as deuterium, i.e. $^{2}H$, may afford certain therapeutic advantages resulting from greater metabolic stability, for example, increased in vivo half-life or reduced dosage requirements, and hence may be preferred in some circumstances.

Substitution with positron-emitting isotopes, such as $^{11}C$, $^{15}O$ and $^{13}N$, can be useful in Positron Emission Topography (PET) studies for examining substrate receptor occupancy.

Isotopically-labelled compounds of formula (I) can generally be prepared by conventional techniques known to those skilled in the art or by processes analogous to those described in the accompanying Examples using an appropriate isotopically-labelled reagent in place of the non-labelled reagent previously employed.

General Synthetic Methods
The compound of formula (Ia) may be synthesized using the process shown generally in Scheme 1.
Scheme 1
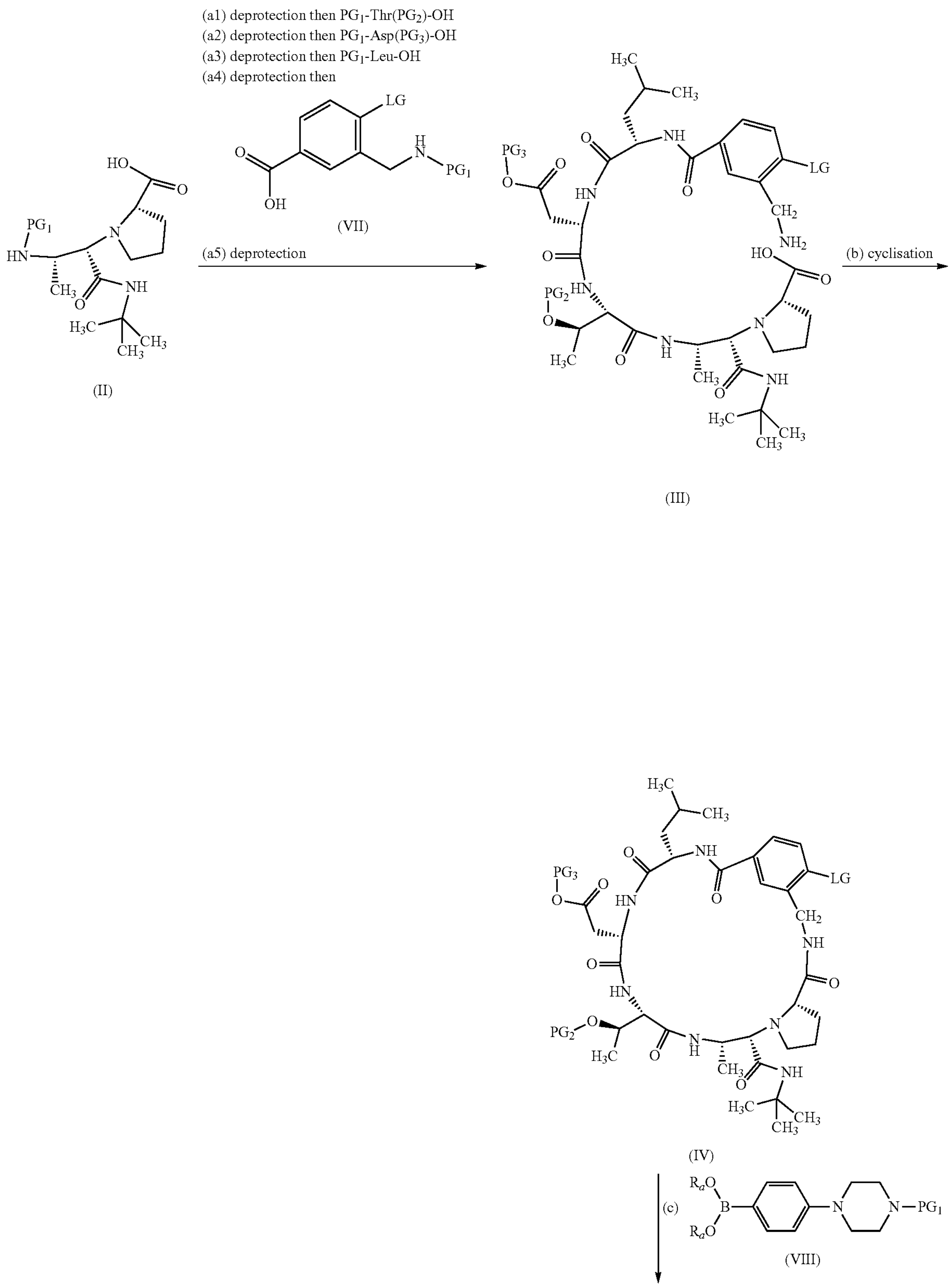
(II)
(VII)
(III)
(IV)
(VIII)

-continued

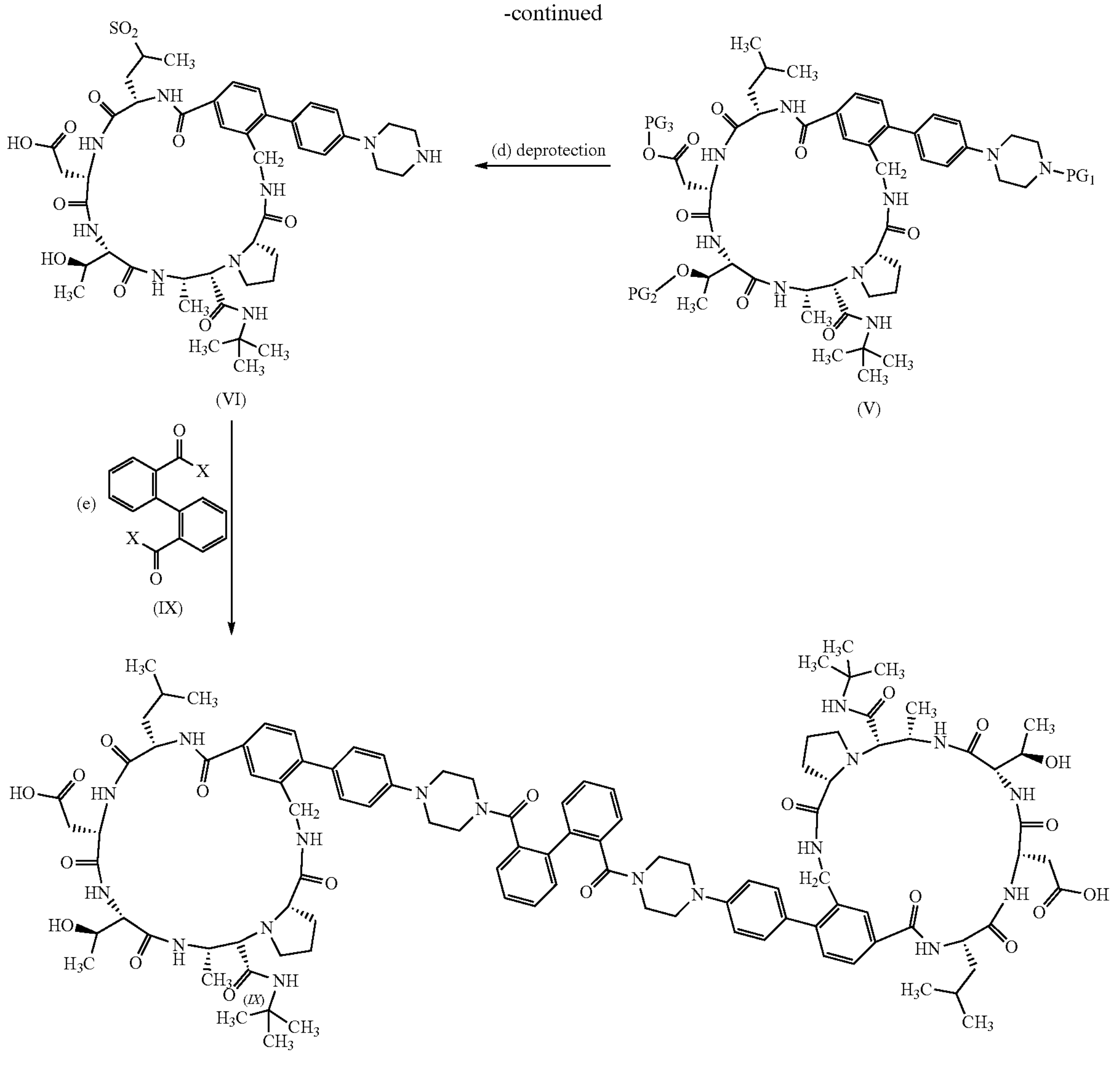

(Ia)

In Scheme 1, the variables have the following meanings:

$PG_1$ is an amino-protecting group;

$PG_2$ is a hydroxy-protecting group;

$PG_3$ is a carboxy-protecting group;

LG is a leaving group;

X is a leaving group or a group convertible to a leaving group; and each $R_a$ is $C_{1-6}$ alkyl, or the two groups $R_a$ together form a $C_{1-6}$ alkylene group optionally fused to an aryl group.

There is no particular limitation to the nature of each of the protecting groups $PG_1$, $PG_2$ and $PG_3$ provided that they fulfil the normal function of a protecting group, i.e. that they can be attached to the relevant group, remain attached so as to protect that group from any subsequent reaction to which they may be labile, and can be removed when protection is no longer required.

The protecting groups $PG_1$, $PG_2$ and $PG_3$ are well known to those skilled in the art. Suitable examples are described in "Protective Groups in Organic Synthesis" by T. W. Greene and P. Wuts, Wiley and Sons, 3rd Edition, 1999.

Examples of the amino-protecting group $PG_1$ include the following: carbobenzyloxy (Cbz); p-methoxybenzyl carbonyl (Moz or MeOZ); tert-butyloxycarbonyl (BOC); 9-Fluorenylmethyloxycarbonyl (Fmoc) group; acetyl (Ac); benzoyl (Bz); benzyl (Bn); carbamate; p-methoxybenzyl (PMB); 3,4-dimethoxybenzyl; p-Methoxyphenyl (PMP); tosyl (Ts); Troc (trichloroethyl chloroformate); nosyl & Nps groups. Preferred $PG_1$ groups are BOC and Fmoc.

Examples of the hydroxyl-protecting group $PG_2$ include ethers, the other moiety of the ether being preferably selected from the following: $C_{1-10}$ alkyl, especially $C_{1-4}$ alkyl; acetyl (Ac); benzoyl (Bz); benzyl (Bn); β-methoxyethoxymethyl (MEM); dimethoxytrityl [bis-(4-methoxyphenyl)phenylmethyl](DMT); methoxymethyl (MOM); methoxytrityl [(4-methoxyphenyl)diphenylmethyl](MMT); β-methoxybenzyl (PMB); methylthiomethyl; pivaloyl (Piv); tetrahydropyranyl (THP); tetrahydrofuranyl (THF); trityl (triphenylmethyl, Tr); ethoxyethyl (EE); and silyl ethers, including trimethylsilyl (TMS), tert-butyldimethylsilyl (TBDMS), tri-iso-propylsilyloxymethyl (TOM), and triisopropylsilyl (TIPS). Preferred $PG_2$ groups include $C_{1-4}$ alkyl and especially tert-butyl.

Examples of the carboxyl-protecting group $PG_3$ include esters, the other moiety of the ester group including branched $C_{3-6}$ alkyl, such as tert-butyl; $C_{3-8}$ cycloalkyl, especially cyclohexyl; benzyl; esters of 2,6-disubstituted phenols (e.g. 2,6-dimethylphenol, 2,6-diisopropylphenol, 2,6-di-tert-butylphenol); silyl esters; and orthoesters. Preferred $PG_3$ groups include branched $C_{3-6}$ alkyl, $C_{5-7}$ cycloalkyl, and benzyl, especially tert-butyl, cyclohexyl and benzyl.

Examples of the leaving group LG include halogen (especially chloro, bromo or iodo) and sulfonate groups (such as methanesulfonate, trifluoromethanesulfonate and β-toluenesulfonate). Preferred are halogen, and especially bromo or iodo.

Examples of the group X are leaving groups, as defined and exemplified above in relation to the group LG. Examples of groups convertible to a leaving group include hydroxyl.

Compound (Ill) is formed from compound (II) by successive amide coupling reactions (a1) to (a4) with the relevant protected amino acid, followed by a final deprotection step (a5).

Each of the steps (a1) to (a4) is carried out by, firstly, removing the protecting group $PG_1$ from the amino terminus of the starting amino acid, then coupling the resulting amine, with the carboxyl portion of the next amino acid, typically in the presence of a conventional coupling agent, typically in the presence of base, in a suitable solvent. Unless the solid-phase synthetic method referred to below is used, the carboxyl terminus of the compound of formula (II) and the intermediates involved in steps (a1) to (a4) must be protected during these amide coupling steps. Suitable carboxyl-protecting groups are as defined and exemplified above in relation to the group $PG_3$.

Methods for carrying out the deprotection steps (a1) to (a5), and suitable deprotecting agents, are well known to the person skilled in the art. Suitable deprotecting agents are described in "Protective Groups in Organic Synthesis", referred to above. By way of example, when $PG_1$ is Fmoc, the deprotecting agent may be piperidine.

The coupling agent may be any agent which facilitates the coupling of a carboxylic acid and an amine to produce an amide. Examples of coupling agents are also well known to the person skilled in the art. Typical coupling agents include carbodiimides such as diisopropylcarbodiimide (DIC) and dicyclohexylcarbodiimide (DCC); aminium and uronium reagents such as 1-[bis-(dimethylamino)methyliumyl]-1H-1,2,3-triazolo[4,5-b]pyridine-3-oxide hexafluorophosphate (HATU), 2-(1H-benzotriazol-1-yl]-1,1,3,3-tetramethyluronium hexafluorophosphate (HBTU) and O-(1H-6-chlorobenzotriazole-1-yl)-1,1,3,3-tetramethyluronium hexafluorophosphate (HCTU), and organophosphate reagents such as 3-(diethoxyphosphoryloxy)-1,2,3-benzotriazin-4(3H)-one (DEPBT). The coupling agent may also be used in conjunction with an additive such as HOBT (1-hydroxy-benzotriazole) or ethyl cyanohydroxyiminoacetate (Oxyma Pure®). DIC, HATU and HBTU are preferred.

The base is not particularly restricted provided it is capable of acting as a base and does not react with the activated amino acid. Examples of suitable bases include tertiary amines, including trimethylamine, triisopropylamine and diisopropylethylamine. Diisopropylethylamine is preferred.

The solvent is not particularly restricted provided it is inert to the reaction and capable of dissolving the reactants to at least some extent. Examples of suitable solvents include: halogenated hydrocarbons, such as dichloromethane (DCM); dimethyl sulfoxide (DMSO); dimethylformamide (DMF); N-methylpyrrolidone (NMP) and mixtures thereof. DCM, NMP and DMF are preferred.

Advantageously, steps (a1) to (a5) are carried out on a solid phase. The support is typically an organic polymer, typically in the form of a resin, having functional groups capable of reacting with one terminus of the peptide chain to facilitate attachment of this end to the chain. Since the peptide remains covalently attached to the support throughout the synthesis, excess reagents and side products can be removed by washing and filtration.

Typically, this involves reacting compound (II) with a suitable solid support, such that the carboxy terminus of compound (II) is conjugated to the solid support; performing the deprotection part of steps (a1) to (a4) by washing the solid support with a suitable deprotecting agent; carrying out the coupling part of steps (a1) to (a4) as described above; performing the deprotection step (a5) by washing the solid support with a suitable deprotecting agent; and finally cleaving the compound from the solid support to yield the compound of formula (III).

Examples of solid phase peptide synthesis and methods of carrying them out are well known to the person skilled in the art, as taught for example in "Solid Phase Synthesis: A Practical Guide", ed. S. Kates & F. Albericio, CRC Press, 2000.

Examples of organic polymers suitable for forming solid support resins include polystyrene, typically cross-linked polystyrene (obtained by co-polymerisation of styrene and divinylbenzene).

The functional group may be any group which allows linking to the organic polymer while allowing the partially protected peptide chain to be assembled thereon, and can be cleaved under conditions which do not affect the side-chain protecting groups. Examples of functional groups with which the organic polymer may be functionalized include triarylmethylhalo, preferably tritylhalo (especially tritylchloro); diarylmethylhalo, especially benzhydrylhalo; halobenzyl; and halomethyl. A polymer functionalised with a tritylhalo group, especially 2-chlorotrityl-resin, is preferred as it permits liberation of the partly protected compound of formula (III).

The initial conjugation of compound (II) to a suitable solid support can be carried out by reacting the compound (II) with the functionalised organic polymer which provides the solid support, in a suitable solvent.

For certain resins, especially triarylmethylhalo resins, the reaction may be carried out in the presence of base. The base must be soluble in the solvent. Examples of suitable bases include. tertiary amines, including trimethylamine, triisopropylamine and diisopropylethylamine, of which diisopropylethylamine are preferred.

The solvent is not particularly restricted provided it is inert to the reaction, is capable of causing the organic polymer resin to swell therein, and capable of dissolving the reactants to at least some extent. Examples of suitable solvents include those defined and exemplified above in relation to steps (a1) to (a4) and mixtures thereof. DCM is preferred.

The final step of cleaving the compound from the solid support to produce the compound of formula (III) can be carried out using a cleaving agent in a suitable solvent. The cleaving agent is typically an acid, which is strong enough and/or present in sufficient concentration to cleave the compound of formula (III) from the solid support while leaving the protecting groups on the compound intact. Particularly preferred is 1,1,1,3,3,3-hexafluoroisopropanol (HFIP).

The solvent is not particularly restricted provided it is inert to the reaction and capable of dissolving the reactants to at least some extent. Examples of suitable solvents include alcohols, such as methanol, ethanol and isopropanol, halogenated hydrocarbons, such as dichloromethane (DCM) and mixtures thereof. DCM is preferred.

In step (b), compound (IV) is formed by cyclisation of compound (III) in an intramolecular amide coupling reaction, typically in the presence of a conventional coupling agent, typically in the presence of base, in a suitable solvent.

The coupling agent may be any agent which facilitates the coupling of a carboxylic acid and an amine to produce an amide. Examples of coupling agents include those defined and exemplified above in relation to steps (a1) to (a4). DIC or DEPBT is preferred.

The solvent is not particularly restricted provided it is inert to the reaction and capable of dissolving the reactants to at least some extent. Examples of suitable solvents include those defined and exemplified above in relation to steps (a1) to (a4) and mixtures thereof. DCM or THF is preferred.

The reaction is typically carried out at high dilution in order that the intramolecular amide coupling required for the cyclisation to take place and result in the compound of formula (IV) predominates over any intermolecular reaction between two molecules of the compound of formula (III). Typically, the reaction is carried out at a dilution between 0.1 mM and 10 mM, preferably 0.2 to 5 mM, more preferably 0.5 to 2 mM.

In step (c), compound (V) is formed by reacting compound (IV) with compound (VIII) in an aryl cross-coupling reaction, typically in the presence of a catalyst, typically in the presence of base, in a suitable solvent.

Compounds of formula (VIII) are commercially available. One such commercially available compound is 4-(4-(benzyloxycarbonyl)-piperazino)phenylboronic acid pinacol ester, where $PG_1$ is benzyloxycarbonyl and the two groups $R_a$ together form a 1,1,2,2-dimethylethylene group.

The catalyst may be any catalyst which is able to catalyse the coupling of an aryl halide or aryl sulfonate (e.g. methanesulfonate or trifluoromethanesulfonate) and an aryl boronic ester to form a carbon-carbon bond between two aryl groups. Examples of catalysts include organopalladium reagents and organonickel reagents, of which tetrakis(triphenylphosphine)palladium (0) is preferred.

The reaction is typically carried out in the presence of a base. Examples of suitable bases include alkali metal carbonates such as sodium carbonate or potassium carbonate; alkali metal phosphates, such as sodium phosphate or potassium phosphate; and alkali metal alkoxides, such as sodium ethoxide or potassium ethoxide. Sodium carbonate is preferred.

The solvent is not particularly restricted provided it is inert to the reaction and capable of dissolving the reactants to at least some extent. Examples of suitable solvents include water; alcohols, such as methanol, ethanol and isopropanol; ethers, such as 1,2-dimethoxyethane (DME); and mixtures thereof. A mixture of water, ethanol and DME is preferred.

In step (d), compound (VI) is formed from compound (V) by removal of the amino-protecting group $PG_1$, the hydroxy-protecting group $PG_2$, and the carboxy-protecting group $PG_3$. This is carried out in the presence of a suitable deprotecting reagent, typically in a suitable solvent.

Methods for carrying out the deprotection step (d), and suitable deprotecting reagents, are well known to the person skilled in the art. Suitable deprotecting reagents are described in "Protective Groups in Organic Synthesis", referred to above. Examples of suitable deprotecting reagents include strong acids, of which trifluoroacetic acid is preferred.

In step (e), compound (I) is formed by an amide coupling reaction of compound (VI) with compound (IX), typically in the presence of base, in a suitable solvent.

To facilitate the reaction, the compound of formula (IX) where X is OH may first be converted to another compound of formula (IX) where X is a leaving group, such as halide and particularly where X is chloro. This is carried out by reacting the compound of formula (IX) where X is OH with a halogenating agent. Examples of suitable halogenating agents include oxalyl chloride, thionyl chloride, phosphorus trichloride and phosphorus pentachloride, of which oxalyl chloride is preferred.

The base is not particularly restricted provided it is capable of acting as a base and does not react with the compound of formula (IX) where X is a leaving group. Examples of suitable bases include those defined and exemplified above in relation to steps (a1) to (a4). Tertiary amines, especially diisopropylethylamine are preferred.

The compound of formula (VII) may be synthesized using the process shown generally in Scheme 2.

Scheme 2

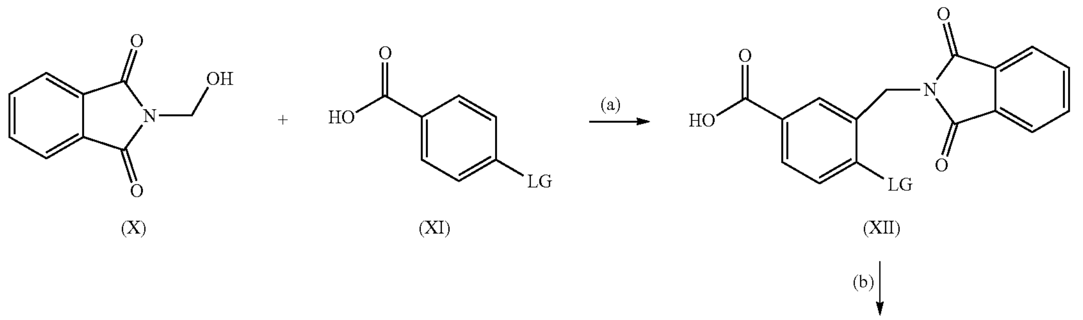

(X) (XI) (XII)

-continued

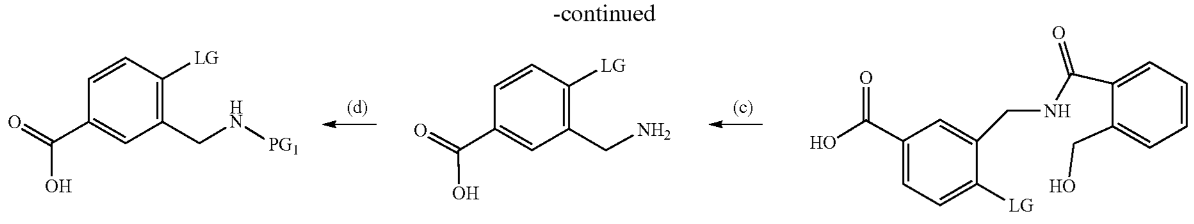

(VII) (XIII) (XII)

In Scheme 2, LG has the same meaning as in Scheme 1.

In step (a), compound (XII) is formed by an esterification reaction of alcohol (X) with carboxylic acid (XI), typically in the presence of an acid, in a suitable solvent. Methods for carrying out the esterification reaction step (a), and suitable conditions agents, are well known to the person skilled in the art. The alcohol (X) and the carboxylic acid (XI) are commercially available.

The acid is not particularly restricted provided it is capable of acting as an acid. Strong acids are typically used. Examples of suitable acids include: inorganic acids such as sulfuric acid and nitric acid, and organic acids, especially sulfonic acids such as methanesulfonic acid, trifluoromethanesulfonic acid, benzenesulfonic acid, and β-toluenesulfonic acid. Sulfonic acids are preferred and trifluoromethanesulfonic acid is especially preferred.

The solvent is not particularly restricted provided it is dissolving the reactants to at least some extent. It is particularly preferred in this case that the acid acts as the solvent. Sulfonic acids are preferred and trifluoromethanesulfonic acid is especially preferred.

In step (b), compound (XIII) is formed by reduction of compound (XII) in a suitable solvent. Methods for carrying out the reduction step (b), and suitable reducing agents, are well known to the person skilled in the art.

The reducing agent may be any agent capable of carrying out the reduction step. Examples of suitable reagents include alkali metal borohydrides such as sodium borohydride and sodium tri(acetoxy)borohydride, of which sodium borohydride is preferred.

The solvent is not particularly restricted provided it is inert to the reaction and capable of dissolving the reactants to at least some extent. Examples of suitable solvents include water; alcohols, such as methanol, ethanol and isopropanol; ethers, such as diethyl ether and 1,2-dimethoxyethane (DME); and mixtures thereof. A mixture of water and isopropanol is preferred.

In step (c), amine (XIV) is formed by cleaving the amide (XIII), typically in the presence of acid, in a suitable solvent. Methods for carrying out the amide cleavage and suitable acids, are well known to the person skilled in the art.

The acid is not particularly restricted provided it is capable of acting as an acid. Strong acids are typically used. Examples of suitable acids include: inorganic acids such as hydrochloric acid, sulfuric acid and nitric acid, and organic acids, especially sulfonic acids such as methanesulfonic acid, trifluoromethanesulfonic acid, benzenesulfonic acid, p-toluenesulfonic acids. Hydrohalic acids are preferred and hydrochloric acid is especially preferred.

The solvent is not particularly restricted provided it is inert to the reaction and capable of dissolving the reactants to at least some extent. Examples of suitable solvents include water; alcohols, such as methanol, ethanol and isopropanol; ethers, such as diethyl ether and 1,2-dimethoxyethane (DME); and mixtures thereof. A mixture of water and isopropanol is preferred.

In step (d), the compound of formula (VII) is formed by attaching a protecting group $PG_1$ to the amine (XIV). Suitable protecting groups, and suitable reagents for their introduction, are well known to the person skilled in the art, and examples are described in "Protective Groups in Organic Synthesis", referred to above. By way of example, when $PG_1$ is Fmoc, a suitable reagent for its introduction may be N-(9H-fluoren-9-ylmethoxycarbonyloxy)succinimide.

Pharmaceutical Compositions

In an aspect of the invention, there is provided a pharmaceutical composition comprising a compound of formula (I) as described herein together with a pharmaceutically acceptable carrier. The pharmaceutical composition may be formulated for any one of oral delivery, topical delivery and parenteral delivery. Examples of pharmaceutical carriers are well known to those skilled in the art.

As used herein, "pharmaceutically acceptable carrier" means any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the pharmacological agent.

Medical Uses and Methods of Treatment

In another aspect, the invention provides the compound of formula (I), or a pharmaceutically acceptable salt or solvate thereof, for use as a medicament.

In another aspect, the invention provides the compound of formula (I), or a pharmaceutically acceptable salt or solvate thereof, for use in treating a condition in a patient associated with a biological function of an α4β7 integrin in a patient.

In another aspect, the invention provides use of the compound of formula (I), or a pharmaceutically acceptable salt or solvate thereof, in the manufacture of a medicament for treating a condition in a patient associated with a biological function of an α4β7 integrin in a patient.

In one aspect of the invention there is provided a method for treating a condition in a patient associated with a biological function of an α4β7 integrin, the method comprising administering to the patient a therapeutically effective amount of the compound of formula (I), or a pharmaceutically acceptable salt or solvate thereof.

In another aspect of the invention, the invention provides the compound of formula (I), or a pharmaceutically acceptable salt or solvate thereof, for use in treating inflammation or an autoimmune disease in a patient. Preferably the inflammation or autoimmune disease is gastrointestinal.

In another aspect of the invention, the invention provides use of the compound of formula (I), or a pharmaceutically acceptable salt or solvate thereof, in the manufacture of a medicament for treating inflammation or an autoimmune disease in a patient. Preferably the inflammation or autoimmune disease is gastrointestinal.

In one aspect of the invention there is provided a method of treating inflammation or an autoimmune disease in a patient, comprising administering to the patient a therapeutically effective amount of the compound of formula (I), or a pharmaceutically acceptable salt or solvate thereof. Preferably the inflammation or autoimmune disease is gastrointestinal.

In some embodiments, the condition or disease is selected from the group consisting of Inflammatory Bowel Disease (IBD), ulcerative colitis, Crohn's disease, celiac disease, microscopic colitis, collagenous colitis, eosinophilic gastroenteritis, pouchitis resulting after proctocolectomy and ileoanal anastomosis, gastrointestinal cancer, cholangitis, pericholangitis, primary sclerosing cholangitis, human immunodeficiency virus (HIV) infection in the GI tract, graft versus host disease, primary biliary sclerosis.

In preferable embodiments, the condition or disease is an inflammatory bowel disease, such as ulcerative colitis or Crohn's disease.

In another aspect of the invention, the invention provides the compound of formula (I), or a pharmaceutically acceptable salt or solvate thereof, for use in treating a viral disease in a patient. Preferably the inflammation or an autoimmune disease is gastrointestinal.

In another aspect of the invention, the invention provides use of the compound of formula (I), or a pharmaceutically acceptable salt or solvate thereof, in the manufacture of a medicament for treating a viral disease in a patient. Preferably the inflammation or an autoimmune disease is gastrointestinal.

In one aspect of the invention there is provided a method of treating a viral disease in a patient, comprising administering to the patient a therapeutically effective amount of the compound of formula (I), or a pharmaceutically acceptable salt or solvate thereof.

In one embodiment, the disease or condition is a local or systemic infection of a virus or retrovirus. In one embodiment, the disease or condition is HIV/AIDS. In one embodiment, the disease or condition is HIV-1. In one embodiment, the disease or condition is HIV-2.

In some embodiments, the compound of formula (I), inhibits binding of $\alpha4\beta7$ integrin to MAdCAM. Preferably, the compound selectively inhibits binding of $\alpha4\beta7$ integrin to MAdCAM.

In any embodiment, the patient is preferably a human.

As used herein, the terms "disease", "disorder", and "condition" may be used interchangeably.

As used herein, "inhibition," "treatment," "treating," and "ameliorating" are used interchangeably and refer to, e.g., stasis of symptoms, prolongation of survival, partial or full amelioration of symptoms, and partial or full eradication of a condition, disease or disorder in a subject, e.g., a mammal.

As used herein, "prevent" or "prevention" includes (i) preventing or inhibiting the disease, injury, or condition from occurring in a subject, e.g., a mammal, in particular, when such subject is predisposed to the condition but has not yet been diagnosed as having it; or (ii) reducing the likelihood that the disease, injury, or condition will occur in the subject.

As used herein, "therapeutically effective amount" refers to an amount effective, at dosages and for a particular period of time necessary, to achieve the desired therapeutic result. A therapeutically effective amount of the pharmacological agent may vary according to factors such as the disease state, age, sex, and weight of the individual, and the ability of the pharmacological agent to elicit a desired response in the individual. A therapeutically effective amount is also one in which any toxic or detrimental effects of the pharmacological agent are outweighed by the therapeutically beneficial effects.

In some embodiments, the compound is administered by a form of administration selected from the group consisting of oral, intravenous, peritoneal, intradermal, subcutaneous, intramuscular, intrathecal, inhalation, vaporization, nebulization, sublingual, buccal, parenteral, rectal, vaginal, and topical.

In some embodiments, the compound is administered as an initial dose followed by one or more subsequent doses and the minimum interval between any two doses is a period of less than 1 day, and wherein each of the doses comprises an effective amount of the compound.

In some embodiments, the effective amount of the compound is the amount sufficient to achieve at least one of the following selected from the group consisting of: a) about 50% or greater saturation of MAdCAM binding sites on $\alpha4\beta7$ integrin molecules; b) about 50% or greater inhibition of $\alpha4\beta7$ integrin expression on the cell surface; and c) about 50% or greater saturation of MAdCAM binding sites on $\alpha4\beta7$ molecules and about 50% or greater inhibition of $\alpha4\beta7$ integrin expression on the cell surface, wherein i) the saturation is maintained for a period consistent with a dosing frequency of no more than twice daily; ii) the inhibition is maintained for a period consistent with a dosing frequency of no more than twice daily; or iii) the saturation and the inhibition are each maintained for a period consistent with a dosing frequency of no more than twice daily.

In some embodiments, the compound is administered at an interval selected from the group consisting of around the clock, hourly, every four hours, once daily, twice daily, three times daily, four times daily, every other day, weekly, bi-weekly, and monthly.

EXAMPLES

The following Examples illustrate the preparation of compounds of the formula (I). The Intermediates illustrate the preparation of suitable intermediates.

$^{1}H$ and $^{13}C$ Nuclear magnetic resonance (NMR) spectra were in all cases consistent with the proposed structures, and were obtained using a 500 MHz Bruker Avance Neo 500 stepctrometer equipped with a 5 mm Probe BBF/H/D probe. Seectra werer recoredet at 40° C. Characteristic chemical shifts (5) are given in parts per million downfield from tetramethylsilane using conventional abbreviations for designation of major peaks: e.g. s, singlet; d, doublet; t, triplet; q, quartet; m, multiplet; b, broad.

Mass spectrometry was performed on a Thermo QExactive MS with electrospray interface with the possibility to perform MSMS experiments.

The following abbreviations are used:

DCM dichloromethane

DIC diisopropylcarbodiimide

DIPEA diispropylethylamine

DMF dimethylformamide
Fmoc-OSu N-(9H-Fluoren-9-ylmethoxycarbonyloxy) succinimide
HATU 1-[Bis-(dimethylamino)methyliumyl]-1H-1,2,3-triazolo[4,5-b]pyridine-3-oxide hexafluorophosphate
HBTU [2-(1H-Benzotriazol-1-yl]-1,1,3,3-tetramethyluronium hexafluoro-phosphate
HFIP 1,1,1,3,3,3-Hexafluoroisopropanol
HOBT 1-Hydroxybenzotriazole
HPLC High-performance liquid chromatography
IPA 2-Propanol
LCMS Liquid chromatography mass spectrometry
TFA Trifluoroacetic acid
THF Tetrahydrofuran Synthesis of intermediates Solid $NaBH_4$ (214 g, 5.65 mol, 5.0 eq.) was then added, with stirring, in small portions over 4 h. The mixture was then stirred overnight at room temperature, turning slowly into a clear solution over this period. LCMS analysis confirmed complete conversion of Intermediate 1 to Intermediate 2. The reaction was quenched through gradual addition of concentrated HCl to a consistent pH value of ~1 (monitoring every 15 minutes with wet pH paper). The resulting cloudy mixture was warmed to ~70° C. for 5 h, affording a clear solution. LCMS analysis confirmed complete conversion of Intermediate 2 to the hydrochloride salt of Intermediate 3. The mixture was left to stir at room temperature overnight and the solvent was then slowly removed under a positive stream of compressed air to give crude Intermediate 3.

Intermediates 1-4

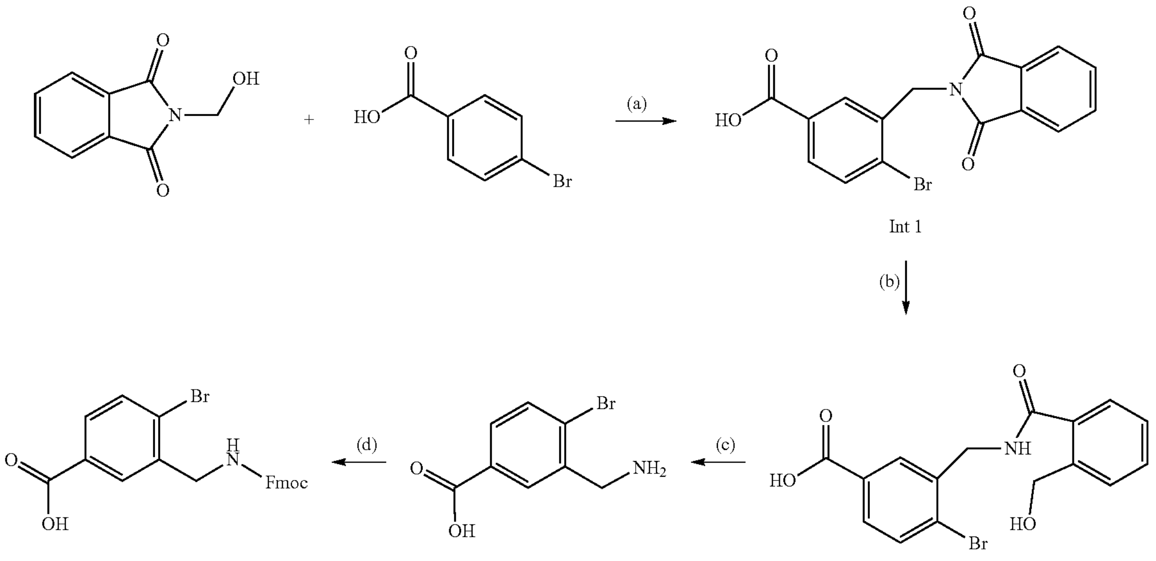

Int 1

Int 4 Int 3 Int 2

Step (a)—Intermediate 1

In a 2.0 L round bottom flask equipped with a stir bar, 4-bromobenzoic acid (227 g, 1.13 mol, 1.0 eq.) was dissolved in trifluoromethanesulfonic acid (1.0 L) and cooled to 0° C. with stirring for 15 minutes. N-(Hydroxymethyl) phthalimide (200 g, 1.13 mol, 1.0 equiv.) was added in portions over 15 minutes. The resulting mixture was stirred at room temperature for 18 h. An LCMS chromatogram of the crude reaction mixture confirmed completion of reaction, as assessed by disappearance of 4-bromobenzoic acid. The mixture was poured into an ice bath (~2.5 L), with stirring. The resulting white solid was filtered and then washed with $H_2O$ until pH of the filtrate reached ~6, as assessed by wet pH paper. The resulting solid was placed under house vacuum to near-dryness to afford crude Intermediate 1.

Steps (b) and (c)—Intermediates 2 and 3

Intermediate 1 (1.13 mol, assuming 100% yield from previous step) was suspended and stirred in a 7:1 isopropanol/$H_2O$ mixture (5.0 L) in a 12.0 L round bottom flask.

Step (c)—Intermediate 4

In the same 12.0 L round bottom flask from step 2, Intermediate 3 (1.13 mol, assuming 100% yield from previous step) was suspended in $H_2O$ (5.0 L). The pH of the mixture was increased to ~8, as assessed by wet pH paper, using triethylamine. A slurry of Fmoc-OSu (381 g, 1.13 mol, 1.0 eq.) in acetonitrile (500 mL) was added in one portion. The mixture was stirred at room temperature for ~65 hours and LCMS analysis confirmed complete consumption of Intermediate 3. The mixture was diluted to ~11 L with $H_2O$, acidified with concentrated HCl to pH ~1, as assessed by wet pH paper, and then stirred for an additional 1.0 h. The resulting suspension was filtered and the solid filter cake washed with water (~2 L). The solid filter cake was triturated with acetonitrile (~3.5 L), filtered again and dried over house vacuum for 2 days to give Intermediate 4 (396.02 g, 0.876 mol, 77% yield over 4 steps from 4-bromobenzoic acid) as an off-white solid. This solid readily dissolved in DMF to a homogeneous solution.

Intermediate 5-9

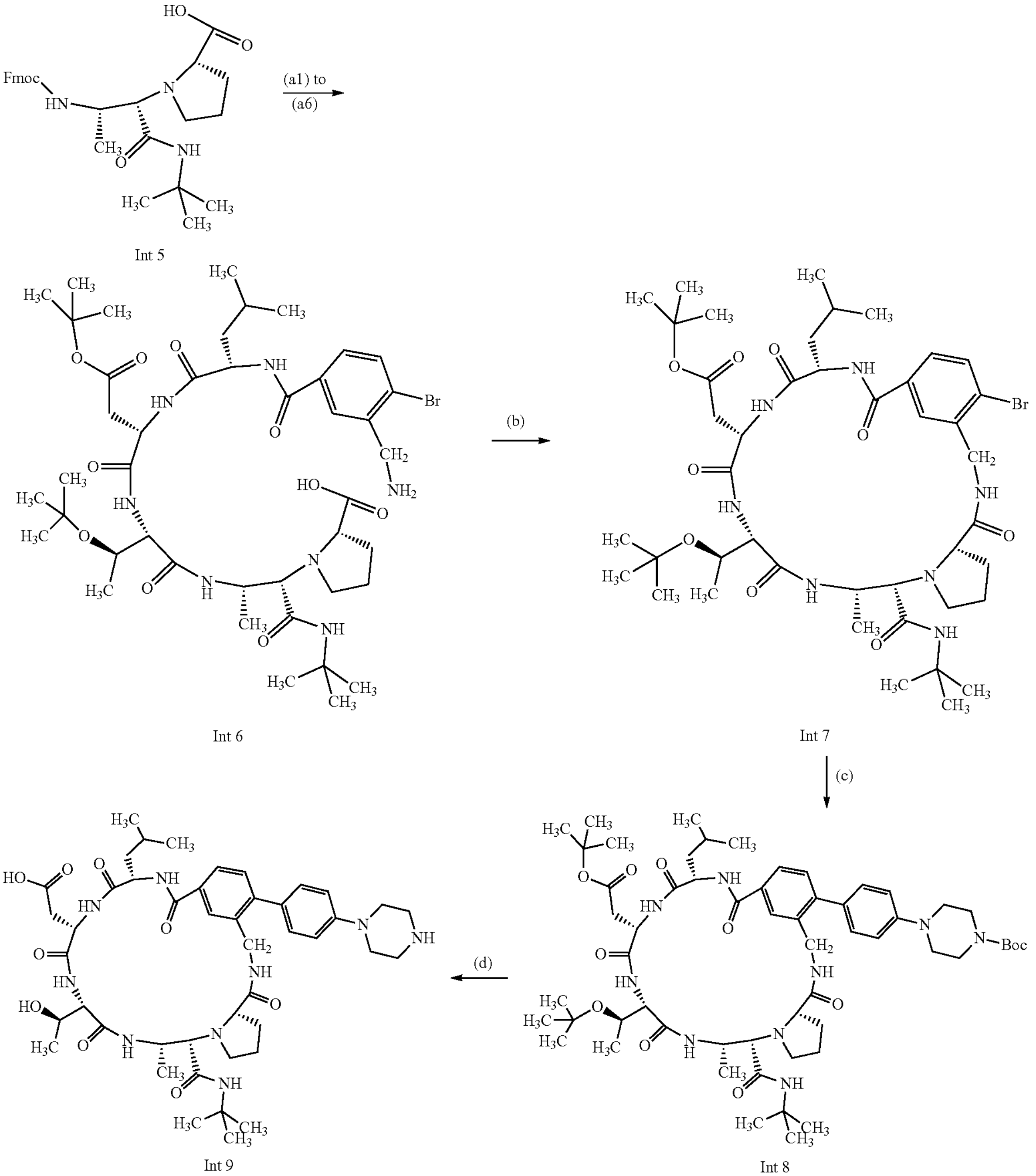

Int 5

Int 6

Int 7

Int 8

Int 9

Steps (a1) to (a6)—Intermediate 6

(a1) To a mixture containing 2-chlorotrityl chloride resin (80 g, 1.0 mmol/g, 80.0 mmol) and Intermediate 5 (disclosed as Compound 4A in WO2017/079821) (1.0 eq) was added DCM (2 L), and DIPEA (4.0 eq) was added dropwise. The resin was mixed for 1.5 hours. Methanol was added (80 mL) and mixed for 30 min, then drained. The Fmoc-protected peptide resin was treated with 20 vol % piperidine in DMF for 30 min.

After this deblocking, the resin was washed with DMF (1 L) 5 times. (a2) Fmoc-L-Thr(tBu)-OH, (2 eq), (a3) Fmoc-L-Asp(tBu)-OH (2 eq), and (a4) Fmoc-L-Leu-OH (2 eq) was coupled subsequently, each using HBTU (2 eq) and DIPEA (3 eq) in DMF (800 mL) for 1 hour and deprotection with 20 vol % piperidine in DMF for 30 min in between.

(a5) Intermediate 4 (1.5 eq) was coupled using HATU (1.5 eq) and DIPEA (3 eq) in DMF (500 mL) for 1 hour. After coupling, the resin was washed with DMF 3 times. The coupling reactions were monitored by ninhydrin color reaction. After the last step, the peptide resin was treated with 20% piperidine in DMF for 30 min. The resin was washed with methanol 3 times, and dried under vacuum.

(a6) The peptide resin was treated with a cleavage cocktail (20 vol % HFIP/80 vol % DCM) for 1 hour and then filtrated. Treatment was repeated once. The combined filtrates were concentrated under reduced pressure to give crude Intermediate 6.

Step (b)—Intermediate 7

Intermediate 6 was dissolved in DCM at 1 mM concentration. HOBT (2 eq) and DIC (2 eq) were added to the solution and stirred for 24 hour at room temperature. The conversion was monitored by LCMS. After complete reaction, the mixture was concentrated under reduced pressure to give crude Intermediate 7.

Step (c)—Intermediate 8

A mixture of Intermediate 7 (1 eq.) and (4-(4-tert-butoxy-carbonyl)piperazino)-phenylboronic acid pinacol ester (commercially available) (2 eq.) was dissolved in a 1,2-dimethoxyethane+ethanol+water mixture (12+3+4/vol+vol+vol) followed by $Na_2CO_3$ (2 eq). The reaction flask was flushed for at least 10 min under nitrogen gas and then $Pd(PPh_3)_4$ (0.4 eq.) was added. The sealed tube was heated to 100° C. and stirred for 24 hours. After cooling, LC-MS analysis confirmed full consumption of reactant and formation of product. The reaction mixture was filtered and the residue washed with THF. The combined filtrates and wash were concentrated under reduced pressure to give crude Intermediate 8 as a pale yellow solid.

Step (d)—Intermediate 9

Intermediate 8 was dissolved in a mixture of TFA+DCM (1+1/vol+vol) and stirred for 1 hour. The mixture was concentrated under reduced pressure to give crude Intermediate 9. The crude compound was purified by a two-step reversed-phase preparatory HPLC procedure. The first step was conducted using eluent A: 0.075 vol % TFA in $H_2O$ and eluent B: acetonitrile. The second step was conducted using eluent A: 0.01 M $NH_4HCO_3$ in $H_2O$ and eluent B: acetonitrile. Purified Intermediate 9 was isolated by lyophilization and was obtained as a white solid.

Example 1

2,2'-((S,S,S,S,S,S,$1^2$,8S,11S,14S,17S,18S)-((([1,1'-biphenyl]-2,2'-dicarbonyl)-bis(piperazine-4,1-diyl)) bis(4,1-phenylene))bis(18-(tert-butylcarbamoyl)-14-((R)-1-hydroxyethyl)-8-isobutyl-17-methyl-2,6,9,12,15-pentaoxo-3,7,10,13,16-pentaaza-1(2,1)-pyrrolidina-5(1,3)-benzenacyclooctadecaphane-$5^6$,11-diyl))-diacetic acid

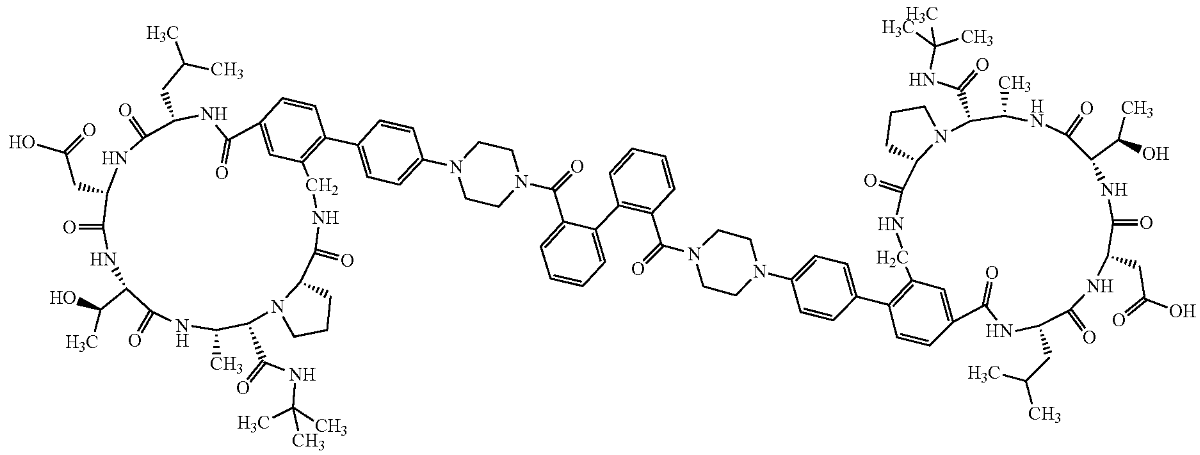 [SMILES: CC(C)C[C@@H]1NC(=O)c2ccc(-c3ccc(N4CCN(C(=O)c5ccccc5-c5ccccc5C(=O)N5CCN(c6ccc(-c7ccc8cc7CNC(=O)[C@@H]7CCCN7[C@H](C(=O)NC(C)(C)C)[C@H](C)NC(=O)[C@H]([C@@H](C)O)NC(=O)[C@H](CC(=O)O)NC(=O)[C@H](CC(C)C)NC8=O)cc6)CC5)CC4)cc3)c(c2)CNC(=O)[C@@H]2CCCN2[C@H](C(=O)NC(C)(C)C)[C@H](C)NC(=O)[C@H]([C@@H](C)O)NC(=O)[C@H](CC(=O)O)NC1=O]

To a solution of diphenic acid (1.0 eq) in anhydrous THF was added oxalyl dichloride (2.5 eq), followed by a catalytic amount of DMF. The suspension was stirred at 25° C. and became a yellow solution over the course of 1 hour. The solvents were removed under reduced pressure to give diphenic acid bis-chloride as a yellow solid.

Diphenic acid bis-chloride was dissolved in anhydrous DCM. Lyophilized Intermediate 9 (2.0 eq) was added to the flask, followed by dropwise addition of DIPEA (25.0 eq). The reaction was monitored by LCMS. After 30 min, the solution was concentrated under reduced pressure to obtain crude compound 1. The crude material was purified by a two-step reversed-phase preparatory HPLC procedure. The first step was conducted using eluent A: 0.075 vol % TFA in $H_2O$ and eluent B: acetonitrile. The second step was conducted using eluent A: 0.01 M $NH_4HCO_3$ in $H_2O$ and eluent B: acetonitrile. The purified compound of Example 1 was isolated by lyophilization and was obtained as a white solid.

Structural Identification of the Compound of Example 1 by MS/MS

The compound was dissolved with Milli-Q water (20%) and 80% acetonitrile with 0.05% formic acid to a concentration of 1 mg/mL followed by direct infusion MS and MS/MS. The experiment was performed on a Thermo QExactive MS with electrospray interface with the possibility to perform MS/MS experiments. The mass scan range was set from 230 to 1730 Da and HCD fragmentation energy varied from 20 to 50. The collection window was +/−2 Da.

The average mass of the compound of Example 1 is 1958.30 Da (mono isotopic mass is 1957.02 Da) and this is primarily detected as the double charged proton adduct. The m/z of the monoisotopic species is 979.52.

Figure 1:
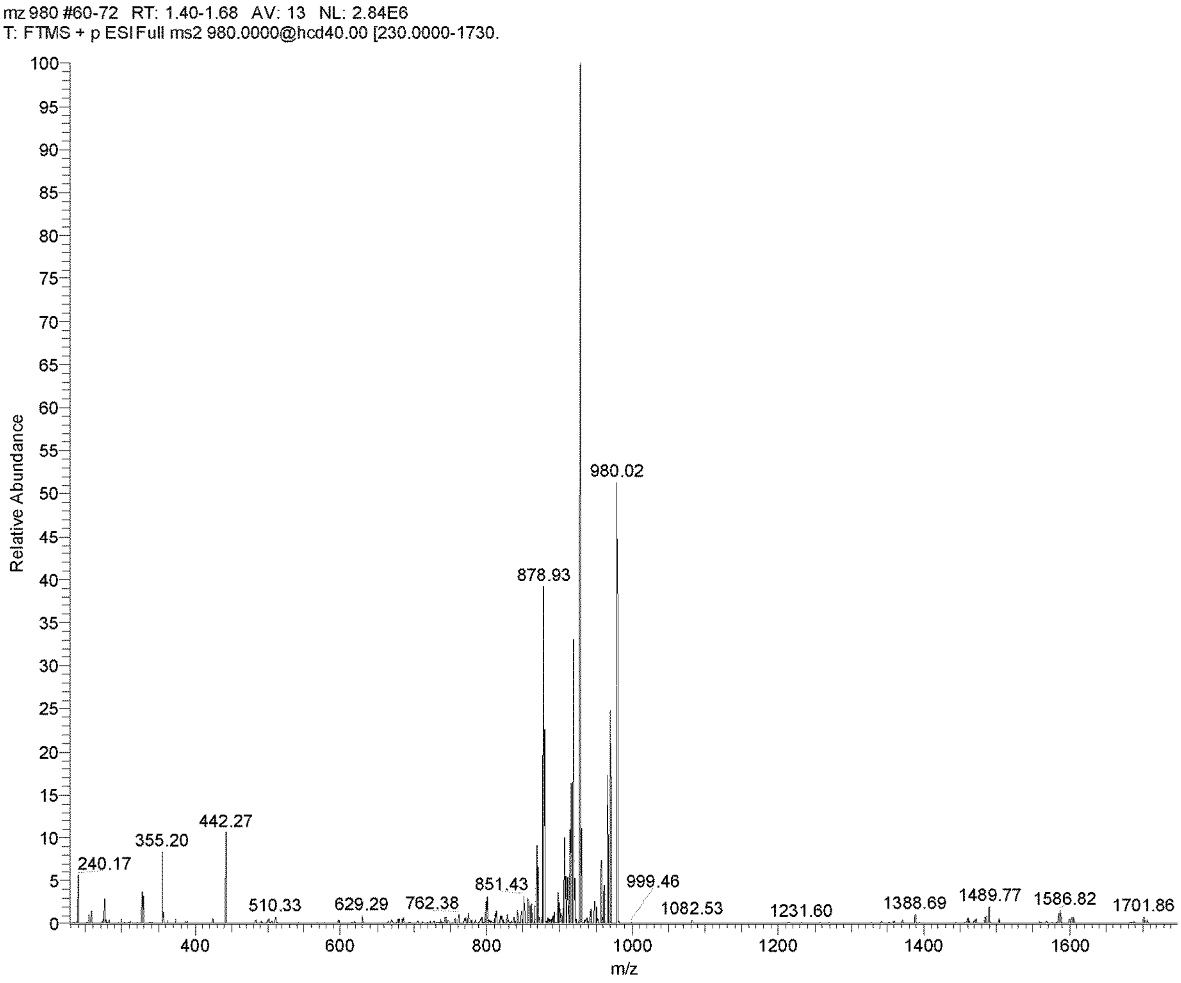
FIG. 1 is an MS/MS spectrum showing the fragmentation of the compound of Example 1 to yield a compound of m/z 980.02.
Figure 2:
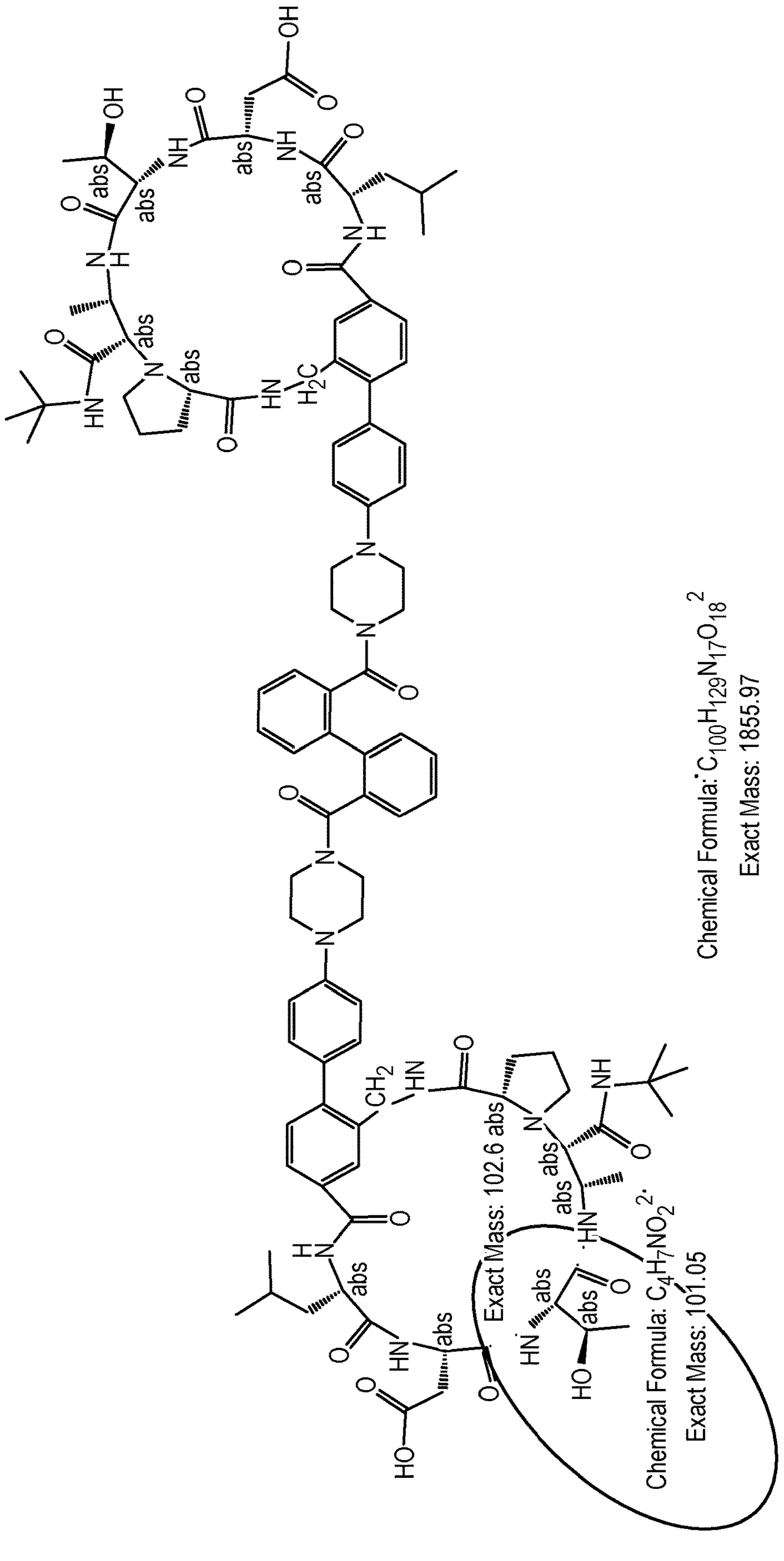
FIG. 2 shows the fragmentation of the compound of Example 1 by the loss of a fragment of 101.05 Da (threonine)
Figure 3:
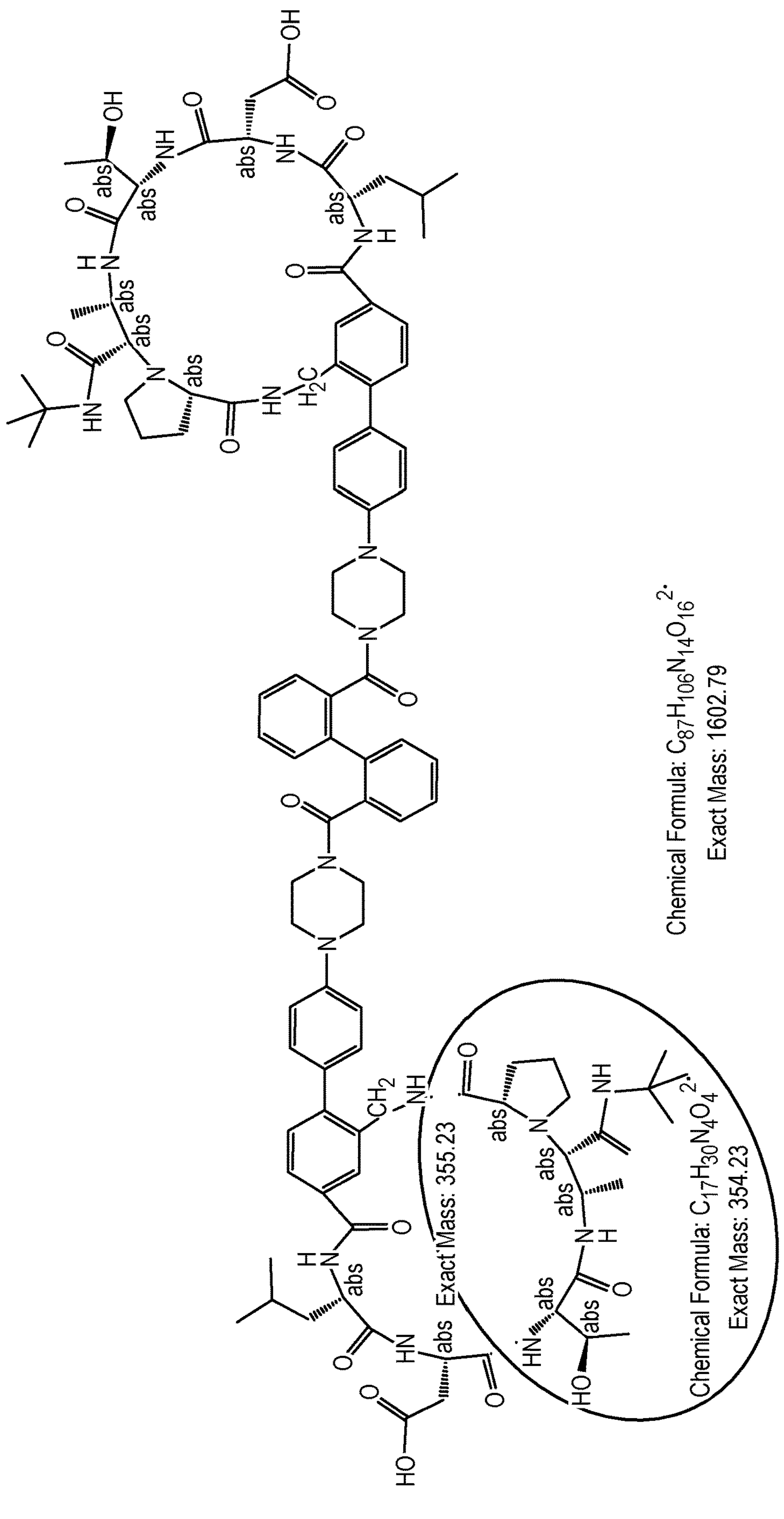
FIG. 3 shows the fragmentation of the compound of Example 1 by the loss of a fragment detected m/z 355.23.
Figure 4:
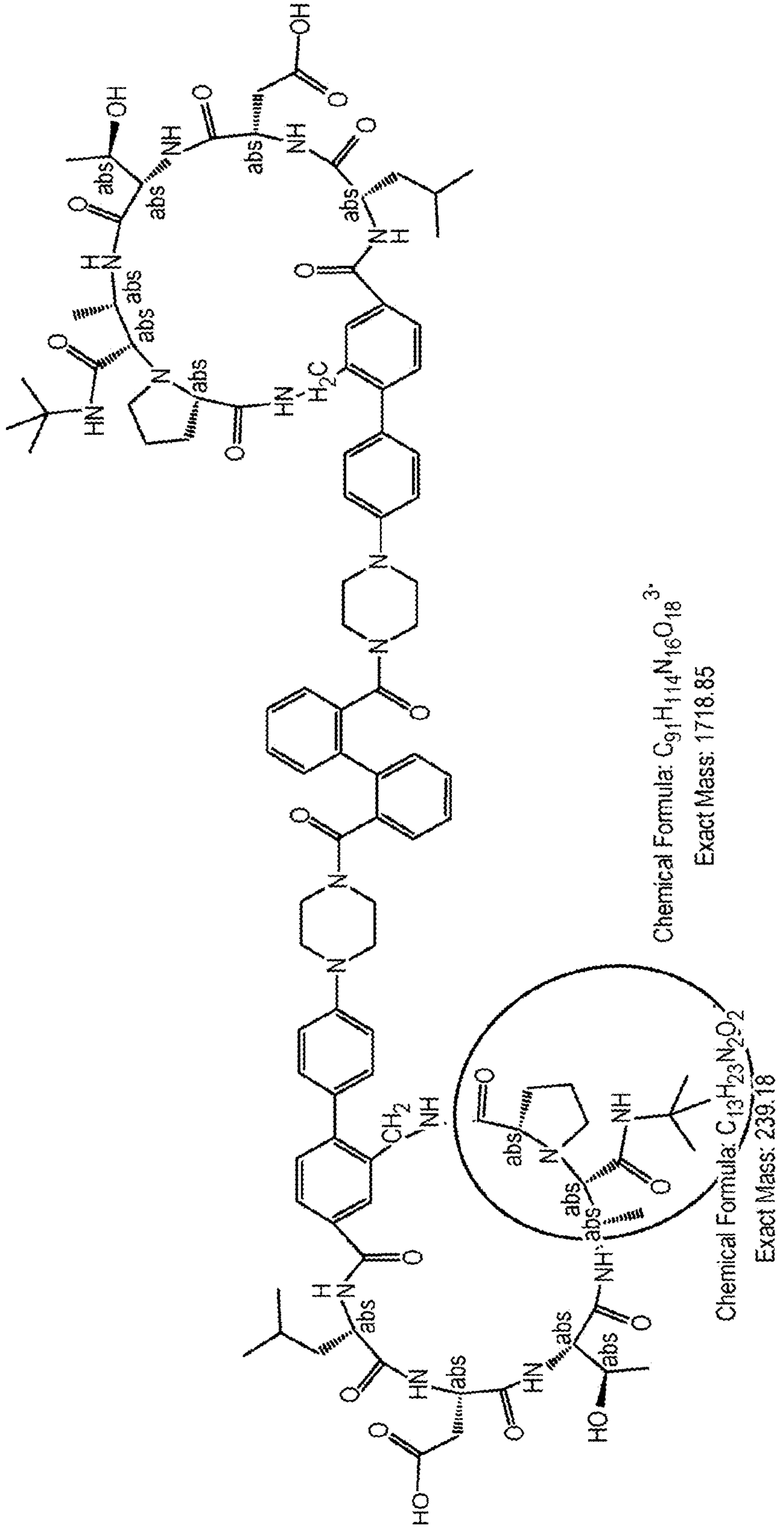
FIG. 4 shows the fragmentation of the compound of Example 1 by the loss of a fragment detected m/z 240.18.
Figure 5:
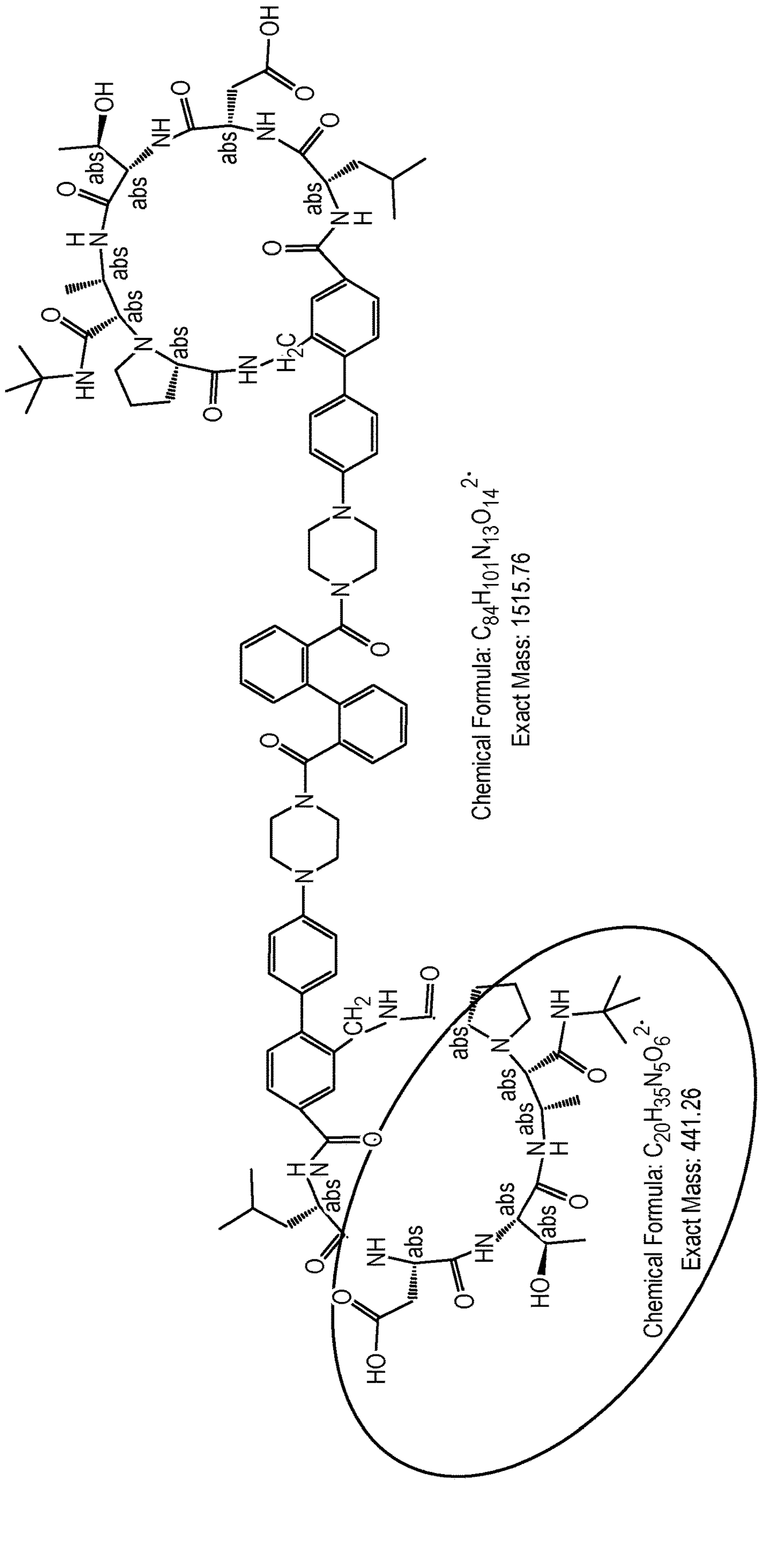
FIG. 5 shows the fragmentation of the compound of Example 1 by the loss of a fragment detected as m/z 442.27.

In order to obtain structural fragmentation, the Higher energy Collisional Dissociation (HCD) of the MS was gradually increased. At a HCD at 40 eV, app 75% of ZP10000 is fragmented. The obtained spectrum is shown in FIG. 1. Two major double charged fragments with monoisotopic m/z of 928.97 and 878.43 are detected (FIG. 2), both indicating a loss of 101.08 Da that corresponds to loss of threonine in the two macrocyclic structures of the compound. The presence of this species is verified by the detection of the remaining part of the molecule (detected as double charged m/z 878.43). Some minor mono charged species are also detected as 240.17, 277.13, 327.24, 355.20, 442.27 Da and only minor mono charged masses higher than 980.02 Da are detected. The likely structures for fragments are given in FIGS. 3 to 5.

NMR data confirms the structure of the molecule.

$^{1}H$ NMR ($d_6$-DMSO, 500 MHz): δ 0.89 (d, J=5 Hz, 6H), 0.94 (d, J=5 Hz, 6H), 0.99 (d, J=5 Hz, 6H), 1.22 (s, 18H), 1.25 (d, J=10 Hz, 6H), 1.54-1.58 (m, 2H), 1.67-1.73 (m, 10H), 1.87 (quint, J=10 Hz, 2H), 2.63-2.73 (m, 4H), 2.91 (t, J=10 Hz, 2H), 3.20 (br s, 4H), 3.26 (d, J=10 Hz, 2H), 3.38 (br s, 4H), 3.51 (dd, J=5, 10 Hz, 2H), 3.57 (q, J=10 Hz, 2H), 3.62 (br s, 4H), 3.88 (br s, 4H), 3.96 (d, J=10 Hz, 2H), 4.08 (dd, J=5, 15 Hz, 2H), 4.22 (hex, J=10 Hz, 2H) 4.30 (dd, J=5, 10 Hz, 2H), 4.36 (m, 2H), 4.60 (dd, J=10.15 Hz, 2H), 4.62-4-65 (m, 2H), 6.95-6.98 (m, 8H), 7.03 (d, J=10 Hz, 2H), 7.25-7.29 (m, 6H), 7.35 (br s, 2H) 7.44 (br s, 2H), 7.46-7.49 (m, 4H), 7.74-7.76 (m, 4H), 8.00 (d, J=5 Hz, 2H), 8.08 (dd, J=5, 10 Hz, 2H), 9.04 (br s, 2H).

$^{13}C$ NMR ($d_6$-DMSO, 125 MHz): δ 19.8 (2C), 20.3 (2C), 21.0 (2C), 23.2 (2C), 24.1 (2C), 24.4 (2C), 28.1 (6 C), 30.7 (2C), 36.1 (2C), 40.1 (2C), 40.7 (4 C), 41.3 (2C), 45.0 (2C), 46.0 (2C), 47.8 (4 C), 50.4 (2C), 51.4 (2C), 52.4 (2C), 57.4 (2C), 64.4 (2C), 65.2 (2C), 67.1 (2C), 115.4 (4 C), 125.4 (2C), 125.6 (2C), 127.4 (2C), 127.6 (2C), 128.7 (2C), 129.5 (2C), 129.6 (6 C), 129.9 (2C), 132.6 (2C), 135.9 (2C), 136.8 (4 C), 143.0 (2C), 149.9 (2C), 166.7 (2C), 168.2 (2C), 168.6 (2C), 169.5 (2C), 170.2 (2C), 171.5 (2C), 174.1 (2C), 174.3 (2C).

Figure 6:
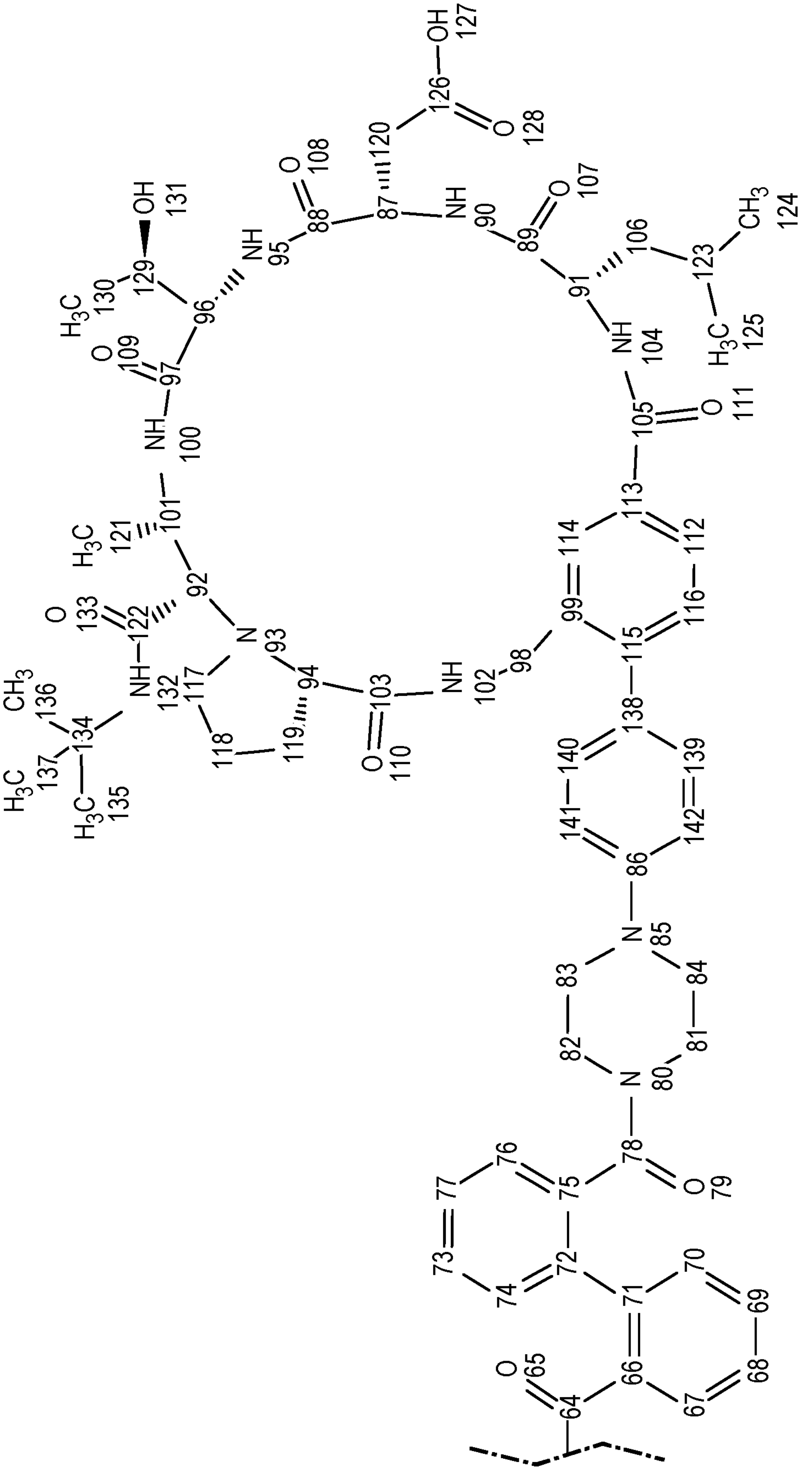
FIG. 6 shows the atom numbers of the compound of Example 1 as assigned by NMR spectroscopy; and (I)
Figure 6:
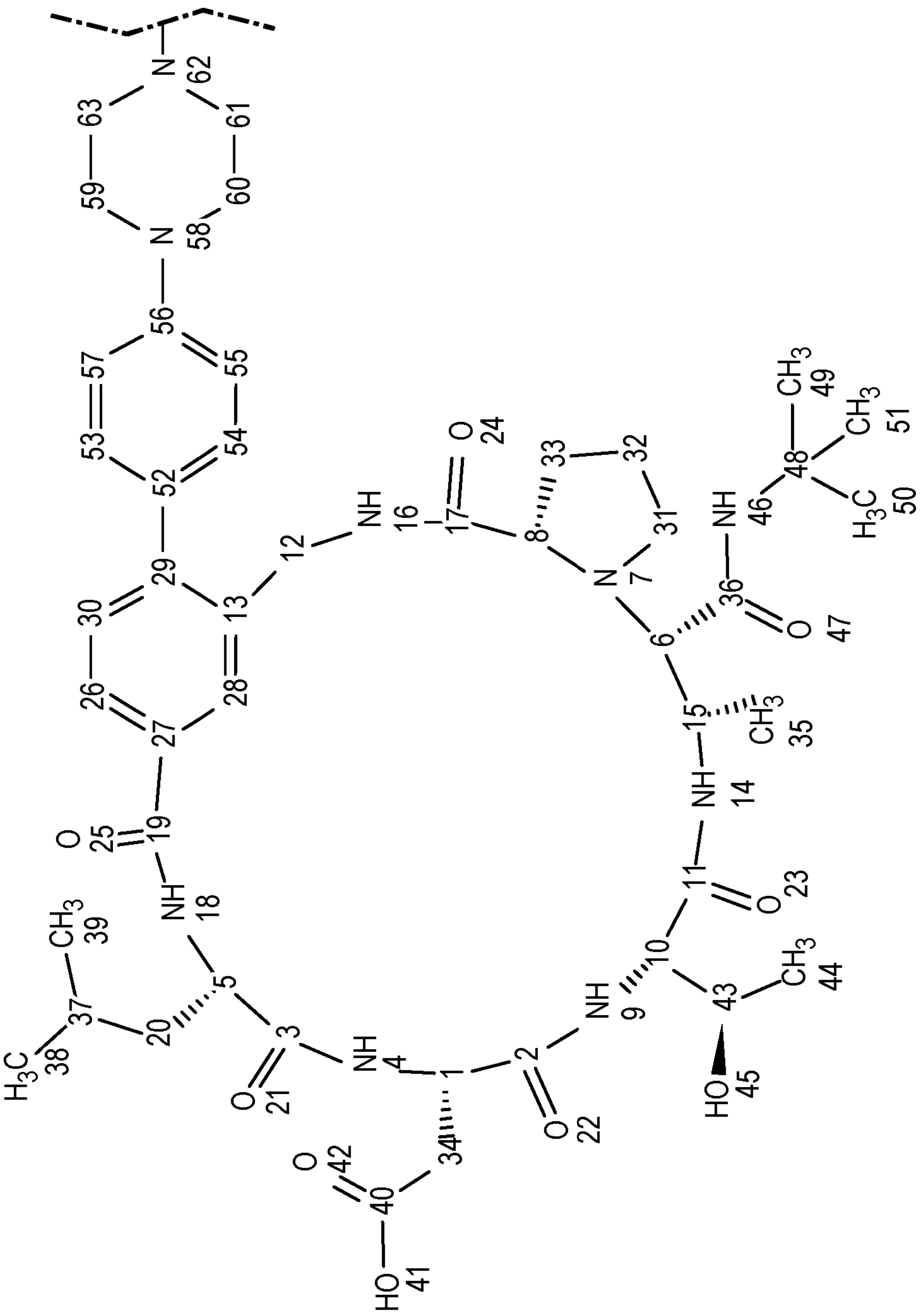

Chemical shift assignment of each atom in DMSO-$d_6$ at 40° C. together with atom numbering used in the assignment for half of the structure of the compound of Example 1 (atoms no. 1-71). This is shown in FIG. 6 and in Table 1 below.

All chemical shifts are given in ppm with an estimated accuracy of ±0.02 ppm for $^{1}H$ chemical shifts and ±0.3 ppm of $^{13}C$ and $^{15}N$ chemical shifts. Referencing is made relative to DMSO for $^{1}H$ and $^{13}C$ (2.50/39.52 ppm) while indirect chemical shift referencing is applied for $^{15}N$ chemical shifts. No stereospecific assignment is made. *Chemical shifts may be interchanged between these carbons. ND=not determined.

TABLE 1

| | $^{1}H$ (ppm) | | $^{13}C$ (ppm) | | $^{15}N$ (ppm) |
|---|---|---|---|---|---|
| Atom | Observed | Predicted | Observed | Predicted | Observed |
| 1, 87 | 4.36 | 4.57 | 52.4 | 50.6 | — |
| 2, 88 | — | — | 170.2 | 173.2 | — |
| 3, 89 | — | — | 174.1 | 171.5 | — |
| 4, 90 | 9.04 | 7.72 | — | — | 118.3 |
| 5, 91 | 4.63 | 4.40 | 51.4 | 53.3 | — |
| 6, 92 | 3.26 | 4.25 | 67.1 | 59.6 | — |
| 7, 93 | — | — | — | — | ND |
| 8, 94 | 3.51 | 3.89 | 64.4 | 61.6 | — |

TABLE 1-continued

| | $^{1}H$ (ppm) | | $^{13}C$ (ppm) | | $^{15}N$ (ppm) |
|---|---|---|---|---|---|
| Atom | Observed | Predicted | Observed | Predicted | Observed |
| 9, 95 | 7.03 | 7.80 | — | — | 102.3 |
| 10, 96 | 3.96 | 4.40 | 57.4 | 59.1 | — |
| 11, 97 | — | — | 168.6 | 171.1 | — |
| 12, 98 | 4.08, 4.60 | 4.33, 4.36 | 39.3 | 41.9 | — |
| 13, 99 | — | — | 136.8 | 125.2 | — |
| 14, 100 | 6.97 | 7.52 | — | — | 123.3 |
| 15, 101 | 4.22 | 4.09 | 45.0 | 52.6 | — |
| 16, 102 | 8.08 | 7.93 | — | — | 110.2 |
| 17, 103 | — | — | 174.3 | 171.6 | — |
| 18, 104 | 8.00 | 8.03 | — | — | 114.3 |
| 19, 105 | — | — | 166.7 | 165.8 | — |
| 20, 106 | 1.69 | 1.68, 1.71 | 41.33 | 39.8 | — |
| 26, 28, | 7.74 | 7.97 | 125.6 | 126.5 | — |
| 112, 114 | — | — | — | — | — |
| 27, 113 | — | — | 129.9 | 127.8 | — |
| 29, 115 | — | — | 143.0 | 135.8 | — |
| 30, 116 | 7.29 | 7.75 | 129.5 | 127.2 | — |
| 31, 117 | 2.91, 3.57 | 2.62, 2.72 | 46.0 | 53.4 | — |
| 32, 118 | 1.55, 1.68 | 1.75, 1.78 | 24.1 | 24.8 | — |
| 33, 119 | 1.67, 1.87 | 1.82, 2.04 | 30.7 | 29.2 | — |
| 34, 120 | 2.68 | 2.51, 2.59 | 36.1 | 39.7 | — |
| 35, 121 | 1.25 | 1.35 | 19.8 | 19.9 | — |
| 36, 122 | — | — | 169.8 | 173.0 | — |
| 37, 123 | 1.73 | 1.80 | 24.4 | 25.8 | — |
| 38, 124 | 0.94 | 0.85 | 21.0 | 22.5 | — |
| 39, 125 | 0.89 | 0.90 | 23.2 | 22.5 | — |
| 40, 126 | | | 171.5 | 176.5 | — |
| 43,129 | 4.30 | 3.91 | 65.2 | 68.1 | — |
| 44, 130 | 0.99 | 1.08 | 20.3 | 19.4 | — |
| 46, 132 | 6.95 | 7.71 | — | — | 144.3 |
| 48, 133 | — | — | 50.4 | 50.0 | — |
| 49, 50, 51 134, 135, 136 | 1.22 | 1.26 | 28.1 | 28.3 | — |
| 52, 135 | — | — | 132.6 | 136.2 | — |
| 53, 54 139, 140 | 7.26 | 7.50 | 129.6 | 126.3 | — |
| 55, 57 141, 142 | 6.98 | 6.86 | 115.42 | 116.8 | — |
| 56, 86 | — | — | 149.9 | 150.3 | — |
| 58, 84 | — | — | — | — | ND |
| 59, 60, 83, 85 | 3.20, 3.38 | 3.20, 3.23 | 47.9 | 48.9 | — |
| 61, 63, 81, 82 | 3.62, 3.88 | 3.62, 3.78 | 40.7 | 46.2 | — |
| 62, 80 | — | — | — | — | ND |
| 64, 78 | — | — | 168.2 | 168.0 | — |
| 66, 75 | — | — | 135.9 | 129.3 | — |
| 67, 74 | 7.44 | 7.73 | 127.6 | 129.0 | — |
| 68, 76 | 7.35 | 7.57 | 129.7 | 128.2 | — |
| 69, 77* | 7.47 | 7.64 | 128.7 | 128.1 | — |
| 70, 73* | 7.47 | 7.74 | 127.4 | 125.1 | — |
| 71, 72 | — | — | 136.8 | 139.1 | — |

Nuclear Overhauser effect (NOE) spectroscopy further confirmed the structure of the molecule. The following sequential key NOE cross-peaks were analysed for verification of the primary structure of the cyclic peptide moiety:

| Nuclear Overhauser effect (NOE) spectroscopy further confirmed the structure of the molecule. The following sequential key NOE cross-peaks were analysed for verification of the primary structure of the cyclic peptide moiety: | |
|---|---|
| NOE correlation | Comment |
| $H^N$ #9 (Thr) - Hα #1 (Glu) | Observed |
| $H^N$ #14 - Hα #10 (Thr) | Observed but overlap with $H^N$ #46 |
| $H^N$ #46 - Hα #6 | Observed but overlap with $H^N$ #14 |
| Hδ #31 (Pro) - Hα #6 | Not observed due to overlap with the residual water signal |
| Hα #8 (Pro) - Hα #6 | Observed (weak) |
| Hβ #33 (Pro) - Hα #6 | Observed (weak) |
| $H^N$ #16 - Hα #8 (Pro) | Observed |
| $H^N$ #18 (Leu) - $H^{Ar}$ #28 | Observed |
| $H^N$ #4 (Glu) - Hα #5 (Leu) | Observed |

The following key NOE and long-range $^1H$-$^{13}C$ (HMBC) cross-peaks were analysed for verification of the atom connectivity of the linking unit:

| The following key NOE and long-range $^1H$-$^{13}C$ (HMBC) cross-peaks were analysed for verification of the atom connectivity of the linking unit: | |
|---|---|
| NOE correlation | Comment |
| $H^{Ar}$ #30 - $H^{Ar}$#53/54 | Not unambiguously observed due to spectral overlap |
| $H^{CH2}$ #12 - $H^{Ar}$ #53/54 | Observed |
| $H^{Ar}$ #53/54 - $H^{CH2}$ #59/60 | Observed |
| $H^{Ar}$ #55/57 - $H^{CH2}$ #59/60 | Observed |
| $H^{Ar}$ #55/57 - $H^{CH2}$ #61/63 | Observed |
| $H^{Ar}$ #67 - $H^{CH2}$ #59/60 | Observed |
| $H^{Ar}$ #67 - $H^{CH2}$ #61/63 | Observed |
| $H^{Ar}$ #68 - $H^{CH2}$ #59/60 | Observed (weak) |
| $H^{Ar}$ #68 - $H^{CH2}$ #61/63 | Observed (weak) |

Long Range $^1H$-$^{13}C$ Correlation

| Long range $^1H$-$^{13}C$ correlation | |
|---|---|
| Long range $^1H$-$^{13}C$ correlation | Comment |
| $H^{Ar}$ #30 - $C^{Ar}$ #13 | Observed |
| $H^{Ar}$ #30 - $C^{Ar}$ #27 | Observed |
| $H^{Ar}$ #30 - $C^{Ar}$ #52 | Observed |
| $H^{Ar}$ #53/54 - $C^{Ar}$ #29 | Observed |
| $H^{Ar}$ #53/54 - $C^{Ar}$ #56 | Observed |
| $H^{Ar}$ #55/57 - $C^{CH2}$ #59/60 | Not observed |
| $H^{CH2}$ #59/60 - $C^{Ar}$ #56 | Not observed due to broad $^1H$ signals |
| $H^{Ar}$ #67 - C═O #64 | Observed |

Example 2

The compound of Example 1 was used in competition assay on CD4+ integrin $\alpha_4$+$\beta_7$-lo memory T cells.

Receptor occupancy in primary cells was determined by measuring the amount of biotinylated human recombinant MAdCAM-1-Fc or human recombinant VCAM-1-Fc bound to selected cell populations using flow cytometry. Human recombinant MAdCAM-1-Fc or human recombinant VCAM-1-Fc (R&D systems) were biotinylated using commercially available reagents and protocol (Pierce).

Whole blood was collected from human donors in sodium heparin tubes. A volume of 100 μL of blood was incubated with the compound of Example 1 and 4 mM $MnCl_2$ for 1 hour at room temperature. Cells were washed twice with 1 mL of 1× Dulbecco's phosphate buffered saline (DPBS) calcium magnesium free (CMF) (ThermoFisher Scientific) and resuspended in 100 μL of DPBS CMF.

Biotinylated human recombinant MAdCAM-1-Fc or VCAM-1-Fc were added at saturating concentration and incubated at room temperature for 1 hour. A volume of 2 mL of 1×BD FACS Lyse (BD Biosciences) was then added and the mixture was incubated for 8-12 minutes at room temperature in the dark to lyse red blood cells. Cells were washed with 1 mL stain buffer-fetal bovine serum (FBS) (BD Biosciences) and resuspended in 100 μL stain Buffer-FBS (BD Biosciences) containing 4 mM $MnCl_2$. Biotinylated-rhMAdCAM-1-Fc or VCAM-1-Fc was applied at a saturating concentration of 1200 ng/mL to compete with test article binding and incubated at room temperature for 1 hour. Cells were then washed with 1 mL stain buffer-FBS and resuspended in 100 μL stain buffer-FBS.

The cells were incubated in the dark for 30 minutes at room temperature with 1 μL Streptavidin APC (Biolegend 0.2 mg/ml) and a panel of antibodies for the detection of memory T helper α4β7-positive cells subset. An amount of 5.0 μL each of the following antibodies were used: CD45 FITC (BioLegend 200 μg/ml), CD29 APC-Cy7 (BioLegend 100 μg/ml), Integrin beta7 PE, (BioLegend concentration 50 μg/mL), CD49d V421 (BioLegend 50 μg/mL), CD3 V510 (BioLegend 30 μg/mL), CD4 PECy7 (BioLegend 100 μg/mL), CD45RO PerCP, BioLegend 200 μg/mL). The cells were then washed with stain-buffer-FBS and resuspended in 150 μL stain buffer-FBS for acquisition on the flow cytometer (BD FACSCanto™ flow cytometer and BDFACSDiva™ software).

Fluorescence-activated cell sorting (FACS) data was acquired by electronic gating on the basis of forward versus side scatter. The cytometer was set to collect 20,000 events in each tube. Cell population were determined using the following markers: CD45+, CD3+, CD4+, CD45RO+, CD49d+, integrin P7, biotinylated ligands.

Compound receptor occupancy was defined as the decrease in the number of integrin $\beta_7$+ or integrin $\beta_7$-lo cells binding biotinylated rhMAdCAM-1 or rhVCAM-1, respectively. Receptor occupancy was calculated with the following equation:

$$100-((\% \text{ ligand-positive cells with compound}/\% \text{ ligand-positive cells DMSO})*100)$$

The ability of the compound of Example 1 to inhibit the binding of labeled human recombinant MADCAM-1 or VCAM was compared with α4β7-positive or α4β7-negative Th memory cells respectively. Whole blood from a single donor was incubated with the compound of Example 1 and saturated amounts of recombinant ligands. The inhibition of MAdCAM or VCAM binding was measured on T cell subsets using FACS analysis. The compound of Example 1 inhibited MAdCAM-1 binding to primary cells with an $IC_{50}$ value of around 87 nM. The compound of Example 1 bound to VCAM with lower affinity, with an $IC_{50}$ value of about 600 nM.

Example 3

In Vivo T Lymphocyte Trafficking Analysis in Mouse Model of Colitis

Animal care: The animal care facility employed is accredited by the Canadian Council on Animal Care (CCAC). This study was approved by a certified Animal Care Committee and complied with CACC standards and regulations governing the use of animals for research. The animals were housed under standardized environmental conditions. A standard certified commercial rodent diet was provided adlibitum. Tap water was provided adlibitum at all times.

Dextran sulfate sodium (DSS) was administered to C57BL/6 female mice for five days through addition to their drinking water at 3%. Body weight and disease activity index ("DAI") were measured on day 5 in order to distribute DSS-treated animals in uniform groups prior to dosing. DAI was scored based on the severity of three specific symptoms associated with colitis: 1—blood in stool (negative hemoccult, positive hemoccult, blood traces in stool visible, rectal bleeding); 2—stool consistency (normal, soft but still formed, very soft, diarrhea); 3—body weight loss.

From day 6 to day 9, the compound of Example 1 or the vehicle were administered orally daily at 5 mL/kg. On day 9, four hours after dosing, the animals were euthanized by cardiac puncture under general anesthesia. Mesenteric lymph nodes (MLN) were collected, triturated, and washed in HBSS-FCS. The cells were incubated for 15 minutes in BD mouse Fc-block followed by 30-minute incubation with specific antibodies. After washes, cells were either fixed using BD fix solution or immediately process for cell surface marker staining. The antibodies used were as followed: CD4 PE (BD Bioscience), CD44 FITC (BD Biosciences), CD45RB PerCy5.5 (BD Biosciences), a4b7 PE (eBiosciences). Cell populations were then analyzed using FACSCanto cytometer and gating on CD4+, CD44 $^{hi}$, CD45RB$^{low}$, α4β7+.

Statistical analysis was performed using GraphPad Prism. Differences among groups were evaluated by two-way ANOVA, with a 95% confidence interval.

In Vivo T Lymphocyte Trafficking Analyses

The ability of several integrin alpha-4-beta-7-inhibiting compounds to attenuate the trafficking of integrin alpha-4-beta-7-expressing T lymphocytes was demonstrated in in vivo pharmacodynamics studies in DSS-treated mice. Dextran Sodium Sulfate (DSS) induces chronic colitis in experimental animals when given orally in drinking water for five days followed by no DSS in drinking water. Chronic inflammation is associated with the infiltration of leucocytes from the blood to intestinal tissues. The interaction between integrin α4β7 and MAdCAM-1 on the endothelium of the gut allows adhesion and trafficking of T cells to the gut. The ability of the compound of Example 1 to attenuate the trafficking of integrin alpha-4-beta-7-expressing T lymphocytes was demonstrated in in vivo pharmacodynamics studies in DSS-treated mice.

The results are shown in FIG. 7. The compound of Example 1 administered at 10, 30 or 100 mg/kg reduced the detection of integrin α4β7+ T helper memory lymphocytes in the mesenteric lymph nodes (MLN). This reduction in α4β7+ T cells in the mesenteric lymph nodes was dose-dependent reaching a reduction of 60% with 100 mg/kg the compound of Example 1.

Example 4

DSS Induced Chronic Colitis

The current study was conducted in the mice model of dextran Sodium Sulfate (DSS) induced ulcerative colitis (UC). DSS induces chronic colitis in experimental animals when given orally in drinking water for 7 days followed by no DSS in drinking water. Chronic intestinal inflammation is associated with body weight loss, diarrhea, blood in the stool and the infiltration of leucocytes from the blood to intestinal tissue. Among those cells, subpopulations of T lymphocytes such as Th1 and Th17 play an important role in the initiation and chronicity of inflammation. Trafficking of T cells from blood to target tissue is a complex process that is controlled by molecularly distinct adhesion and signaling steps. As such, the α4β7 and MAdCAM-1 adhesion mechanism may be closely involved in lymphocyte trafficking to the site of inflammation in the gut.

Evaluation of the therapeutic potential of the compound of Example 1 (cpd 1) in a mouse model of Dextran Sodium Sulfate (DSS) induced ulcerative colitis (UC)

Animals

Female C57Bl/6 mice (Charles River, St-Constant, Qc), weighting 15-20 g at delivery were used for this study. Following arrival in the animal facility, all animals were subjected to a general health evaluation. An acclimation period of 6 days was allowed before the beginning of the study.

Animal Care Committee

TransBIOTech animal care facility is accredited by the Canadian Council on Animal Care (CCAC). This study was approved by the Cegep Levis-Lauzon Animal Care Committee and it complied with CACC standards and regulations governing the use of animals for research.

Housing Environment

The animals were housed under standardized environmental conditions. The mice were housed in auto-ventilated cages, 2-3 per cage. Each cage was equipped with a manual water distribution system. A standard certified commercial rodent diet was provided ad libitum. Tap water was provided ad libitum at all times. It is considered that there are no known contaminants in the diet and water that would interfere with the objectives of the study. Each cage was identified for the corresponding group, indicating the treatment and the identity of the animals housed in the cage. Mice from different treatment groups were not mixed. The animal room was maintained at a controlled temperature of 21.5±1° C. and a relative humidity of 40±20%. A controlled lighting system assured 12 hours light; 12 hours dark per day to the animals. Adequate ventilation of 8-10 air changes per hour was maintained.

Induction of Ulcerative Colitis in C57Bl/6 Mice

Experimental UC was induced in mice by the administration of 3.0% (w/v) DSS (no lot: Q8378) from MP Biomedicals in their drinking water for 7 days. On day 8, DSS drinking water was replaced with regular water until the end of the study.

Oral Dosing of the Test Article and the Vehicle

During the study, cpd 1 or vehicle were administered once every day from day 0-14. The studied compound and the vehicle were dosed orally at 5 mL/kg. Dosing volume was individually adjusted according to the body weight of each animal to reach the target dose of 100 mg/kg. Dosing solutions were freshly prepared every day.

Study design

| Group | animals/ group | DSS in water | Treatment | Dose (mg/kg) | Administration test substance |
|---|---|---|---|---|---|
| 1 | 4 | none | Vehicle p.o. | 0 | From Day 0-14 |
| 2 | 12 | yes | Vehicle p.o. | 0 | From Day 0-14 |
| 3 | 12 | yes | cpd 1 | 100 | From Day 0-14 |

p.o. = per os

| Preparation of test compound and vehicle | | |
|---|---|---|
| Test substance | Solution | Storage |
| Vehicle | 25% Maisine CC/65% Capmul MCM/10% Labrasol | 25° C. |
| cpd 1 | 40 mg/mL in 25% Maisine CC/65% Capmul MCM/10% Labrasol | 4° C. |

Between 18-20 hours before treatment administration, freshly weighted amount of cpd 1 were solubilized with vehicle for a final concentration of 40 mg/ml and was stirred at 37° C. Prior to dosing, formulated cpd 1 was diluted 1:1 with sterile water to a final concentration of 20 mg/ml and sonicated for an additional 15 minutes. The vehicle was also diluted 1:1 in sterile water. The dispersed material was vigorously vortexed prior the dosing of each animal.

Disease Activity Index (DAI) Assessment

Specific symptoms associated to UC were scored based on the severity of each particular symptoms:

1—blood in stool (negative hemoccult, positive hemoccult, visible blood traces in stool, rectal bleeding);

2—stool consistency (normal, soft, diarrhea);

3—body weight loss (score 0: 0-1%; 1: 1.5-5%; 2: 5.5-10%; 3: 10.5-15%; 4: 15.5-20%; 5: >20%).

The overall DAI score was the sum of the three parameters (maximum score 10). Body weight and DAI assessment were performed on Day 0, 2, 4, 6, 8, 9, 10, 12 and 14.

Macroscopic Inflammation Score

Once the mouse was euthanized, the colon was collected, and its length was measured. Lesion length was also measured. Colon lesions was scored macroscopically based on inflammation, thickening and vascularization to give an overall macroscopic inflammation score of each animal in the study. The score in each category is from 0-3, where 0 is none and 3 is worst.

Collection of Samples

On Day 14, 4 hours after cpd 1 and vehicle dosing, the animals were euthanized by cardiac puncture under general anesthesia, according to the "Guide to the Care and Use of Experimental Animals" published by the CCAC.

Blood was transferred to a Sarstedt tube containing heparin. Blood samples were centrifuged at 10000 rpm for 10 min at 4° C. and plasma was transferred into a MAXrecovery tube and put on dry ice. Colon sections were collected for bioanalysis, MPO measurements and for histology.

Results

All results are expressed in graph as mean±standard deviation (SD) of 4-12 mice per group.

The DAI score was assessed individually based on the severity of three specific symptoms: blood in stool, stool consistency and body weight loss. As shown in FIG. 8, DAI score increased following the administration of DSS in drinking water (DSS+vehicle and DSS+cpd 1) and the DAI score was significantly increased in the two DSS groups compared to the vehicle control group from day 4. The administration of the cpd 1 did not lead to any beneficial effect on DAI (FIG. 8).

FIG. 8 shows DAI score is expressed as mean±SD for each group. Statistical differences among groups were determined using a two-way ANOVA, followed by a post-hoc analysis, using Tukey's multiple comparison test, to compare each group to the DSS+vehicle control group. The "ab" in the figure refers to significant difference between no DSS+vehicle group and a: DSS+vehicle group and b: DSS+cpd 1. $p<0.05$.

The macroscopic inflammation score of the colon was scored based on severity of oedema and ulceration after euthanization at termination. The results are presented in FIG. 9. No macroscopic inflammation score was observed in vehicle treated animals. In contrast a macroscopic inflammation score was observed in the two DSS treated groups, confirming DSS induced inflammation of the colon. Interestingly, a significant difference in macroscopic inflammation score was observed between the DSS+vehicle and the DSS+cpd 1 treated mice and the macroscopic inflammation score was around 30% less in the DSS+cpd 1 treated mice, suggesting a therapeutic effect of cpd 1 on intestinal inflammation.

FIG. 9 shows Macroscopic inflammation score calculated for the different groups of DSS induced UC mice, receiving the vehicle or the treatments. Macroscopic inflammation score is expressed as mean±SD, for each group. Statistical differences between the two DSS groups were determined using two-sided unpaired students t-test, with Welsh correction, 95% confidence level. The % reduction of inflammation in the DSS+cpd 1 treated group compared to the DSS+vehicle treated group was calculated by the following formula: (1—(mean DSS+cpd 1/mean DSS+vehicle))×100.

Infiltration of activated neutrophils in tissue results in the release of the enzyme Myeloperoxidase (MPO) into the extracellular space during degranulation. This enzyme plays a key role in immune defense, but it also contributes to tissue damages in the ulcerative colitis immune response. Considering that the exposure to DSS in drinking water induces a pronounced colon inflammation, MPO activity in colon tissue homogenates was quantified by ELISA and expressed per gram colon protein. The results are shown in FIG. 10.

No statistically significant difference in MPO levels was observed between the groups, but a tendency of reduced inflammation in the DSS+cpd 1 group was observed since approximately 49% less MPO U/g colon protein was seen in DSS+cpd 1, when comparing the mean levels of MPO U/g colon protein between the DSS +vehicle and the DSS+cpd 1 groups (FIG. 10).

FIG. 10 shows MPO activity from medio-distal part of the colon. Data are expressed as MPO activity in unit/g colon protein. MPO activity is expressed as mean±SD, for each group. Test for statistical differences among groups were determined using a one-way ANOVA, followed by a post-hoc analysis, using a Tukey's multiple comparison test. The % reduction of MPO levels (U/g) of mean values between DSS+cpd 1 and DSS+vehicle group was calculated by the following formula: (1—(mean DSS+cpd 1/mean DSS+vehicle))×100.

Together, these findings confirm that cpd 1 dosed orally can modify inflammation in a therapeutic model of DSS induced colitis in mice.

All publications mentioned in the above specification are herein incorporated by reference. Various modifications and variations of the present invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications and equivalents of the described modes for carrying out the invention which are obvious to those skilled in chemistry, pharmacy or related fields are intended to be within the scope of the following claims.

The invention claimed is:

1. A compound of formula (I):

(I)

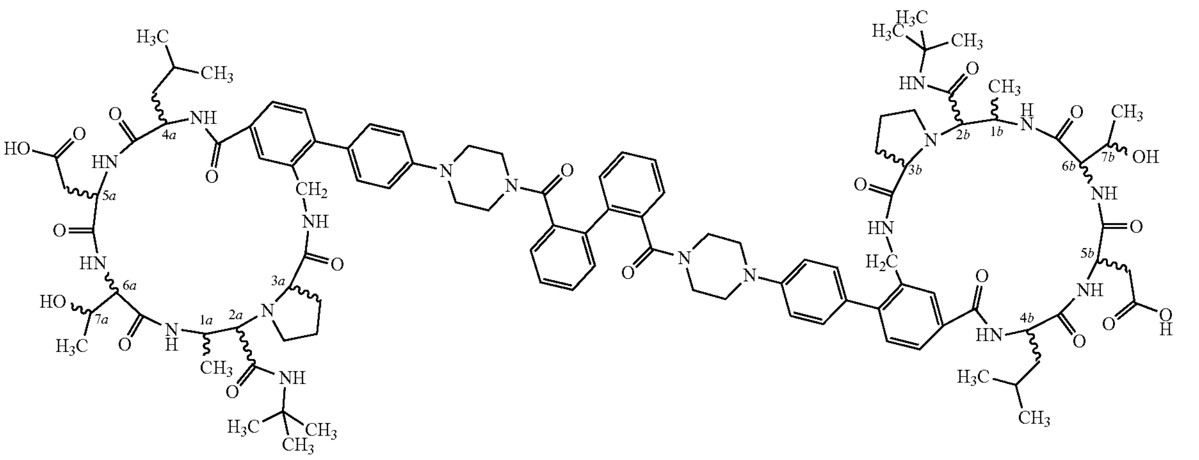

or a pharmaceutically acceptable salt or solvate thereof, wherein the stereochemistry of the carbon atom at each of positions 1a, 1b, 2a, 2b, 3a, 3b, 4a, 4b, 5a, 5b, 6a, 6b, 7a and 7b may each be independently (R) or (S).

2. The compound or pharmaceutically acceptable salt or solvate thereof of claim 1, wherein the stereochemistry of the carbon atom at each of positions 1a and 1b is (S).

7. The compound or pharmaceutically acceptable salt or solvate thereof of claim 1, wherein the stereochemistry of the carbon atom at each of positions 6a and 6b is (S).

8. The compound or pharmaceutically acceptable salt or solvate thereof of claim 1, wherein the stereochemistry of the carbon atom at each of positions 7a and 7b is (R).

9. The compound of claim 1 having formula (Ia):

(Ia)

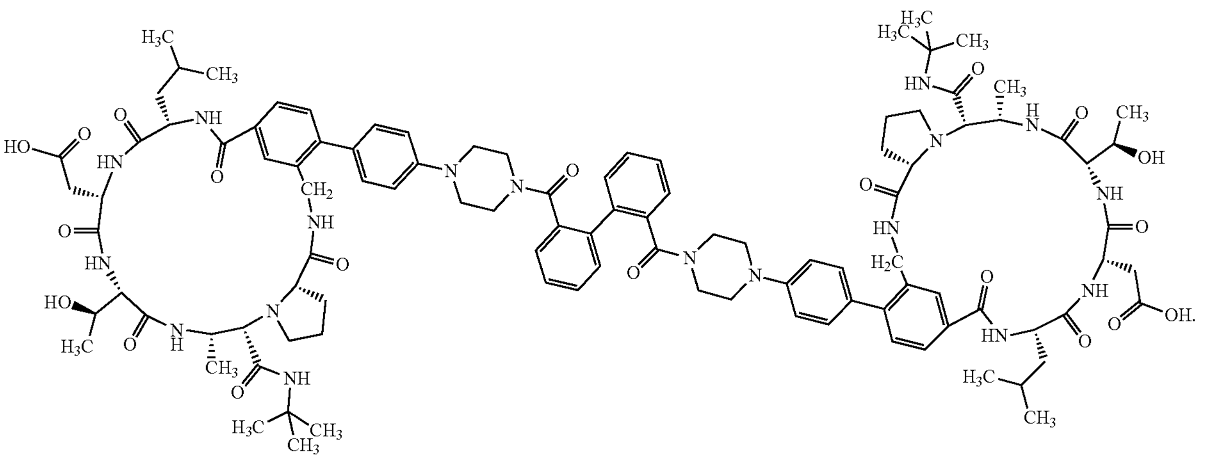

3. The compound or pharmaceutically acceptable salt or solvate thereof of claim 1, wherein the stereochemistry of the carbon atom at each of positions 2a and 2b is (S).

4. The compound or pharmaceutically acceptable salt or solvate thereof of claim 1, wherein the stereochemistry of the carbon atom at each of positions 3a and 3b is (S).

5. The compound or pharmaceutically acceptable salt or solvate thereof of claim 1, wherein the stereochemistry of the carbon atom at each of positions 4a and 4b is (S).

6. The compound or pharmaceutically acceptable salt or solvate thereof of claim 1, wherein the stereochemistry of the carbon atom at each of positions 5a and 5b is (S).

or pharmaceutically acceptable salt or solvate thereof.

10. A pharmaceutical composition comprising the compound or pharmaceutically acceptable salt or solvate thereof of claim 1, and a pharmaceutically acceptable carrier.

11. A method of treating inflammation or an autoimmune disease in a patient in need of said treatment, the method comprising administering to the patient a therapeutically effective amount of the compound or pharmaceutically acceptable salt or solvate thereof of claim 1.

12. The method of claim 11, wherein the inflammation or autoimmune disease is gastrointestinal.

13. A method of treating a condition in a patient, the condition selected from the group consisting of Inflammatory Bowel Disease (IBD), ulcerative colitis, Crohn's disease, celiac disease, microscopic colitis, collagenous colitis, eosinophilic gastroenteritis, pouchitis resulting after proctocolectomy and ileoanal anastomosis, gastrointestinal cancer, cholangitis, pericholangitis, primary sclerosing cholangitis, human immunodeficiency virus (HIV) infection in the GI tract, graft versus host disease, and primary biliary sclerosis, the method comprising administering to the patient a therapeutically effective amount of the compound or pharmaceutically acceptable salt or solvate thereof of claim 1.

14. The method of claim 13, wherein the condition is Inflammatory Bowel Disease (IBD).

15. The method of claim 13, wherein the condition is ulcerative colitis.

16. The method of claim 13, wherein the condition is Crohn's disease.

17. A method of treating a local or systemic infection of a virus or retrovirus in a patient, the method comprising administering to the patient a therapeutically effective amount of the compound or Pharmaceutically acceptable salt or solvate thereof of claim 1.

18. The method of claim 17, wherein the virus is HIV.

* * * * *